US012605061B2

(12) United States Patent
Bhatt et al.

(10) Patent No.: US 12,605,061 B2
(45) Date of Patent: Apr. 21, 2026

(54) EYE IMAGING SYSTEM AND FUNDUS CAMERA POSITIONING DEVICE

(71) Applicant: Agnya Perceptive Solutions, L.L.C., Woodbury, MN (US)

(72) Inventors: Sanjiv Bhatt, San Jose, CA (US);
Saurin Shah, Woodbury, MN (US);
Dmitriy Yam, San Jose, CA (US)

(73) Assignee: Agnya Perceptive Solutions, L.L.C., Woodbury, MN (US)

( * ) Notice: Subject to any disclaimer, the term of this patent is extended or adjusted under 35 U.S.C. 154(b) by 513 days.

(21) Appl. No.: 18/161,404

(22) Filed: Jan. 30, 2023

(65) Prior Publication Data

US 2023/0181026 A1 Jun. 15, 2023

Related U.S. Application Data

(63) Continuation-in-part of application No. 17/664,993, filed on May 25, 2022, now Pat. No. 11,564,568.

(Continued)

(51) Int. Cl.
*A61B 3/00* (2006.01)
*A61B 3/117* (2006.01)
(Continued)

(52) U.S. Cl.
CPC ............ *A61B 3/0025* (2013.01); *A61B 3/117* (2013.01); *A61B 3/12* (2013.01); *A61B 3/16* (2013.01);
(Continued)

(58) Field of Classification Search
CPC ......... A61B 3/0025; A61B 3/117; A61B 3/12; A61B 3/16; A61B 3/0083; G16H 30/40;
(Continued)

(56) References Cited

U.S. PATENT DOCUMENTS 8,896,682 B2 11/2014 Bressler et al.
10,376,142 B2 8/2019 Dirghangi et al.
(Continued)

FOREIGN PATENT DOCUMENTS

KR 101977645 B1 6/2019
WO WO-2017195223 A1 * 11/2017 ............... A61B 3/10
WO WO-2021021657 A1 2/2021

OTHER PUBLICATIONS

"3D lattice structures: Design elements and mechanical responses", Fast Radius, [Online]. Retrieved from the Internet: <URL: https://www.fastradius.com/resources/3d-lattice-design-elements/>, (Accessed Jun. 1, 2022), 7 pgs.

(Continued)

*Primary Examiner* — Mohammed A Hasan
(74) *Attorney, Agent, or Firm* — Schwegman Lundberg & Woessner, P.A.

(57) ABSTRACT

An eye imaging system can include a head-wearable eye imager positioning helmet with an outer shell and a conformable liner that can include head location fiducials defining a specified plane. An attached articulating eye imager fixture can include an eye imager positioning indication system to indicate a position of the eye imager with respect to an eye of the patient for acquiring one or more images at the indicated position such that images recorded over a chronic period of time are assessable using the position information. The articulating eye imager fixture can include an articulating arm and an eye imager mount. The system can assist the patient with helmet positioning, and can automatically position a fundus camera or other eye imager for accurate image capture and analysis, such as using a trained machine learning model for patient evaluation, monitoring, or diagnosis.

20 Claims, 18 Drawing Sheets

Related U.S. Application Data

(60) Provisional application No. 63/202,045, filed on May 25, 2021.

(51) Int. Cl.

| | |
|---|---|
| *A61B 3/12* | (2006.01) |
| *A61B 3/16* | (2006.01) |
| *G16H 30/40* | (2018.01) |
| *G16H 40/67* | (2018.01) |
| *G16H 50/30* | (2018.01) |

(52) U.S. Cl.
CPC ............. *G16H 30/40* (2018.01); *G16H 40/67* (2018.01); *G16H 50/30* (2018.01)

(58) Field of Classification Search
CPC ........ G16H 40/67; G16H 50/30; G16H 30/20; G16H 40/63; G16H 50/20
USPC ........................................................ 351/206
See application file for complete search history.

(56) References Cited

U.S. PATENT DOCUMENTS

| | | | | |
|---|---|---|---|---|
| 10,413,180 | B1 | 9/2019 | Barriga et al. | |
| 10,542,885 | B2 | 1/2020 | Fletcher et al. | |
| 10,722,180 | B2 | 7/2020 | Zhang et al. | |
| 11,564,568 | B1 * | 1/2023 | Bhatt | A61B 3/14 |
| 12,066,725 | B2 * | 8/2024 | Lee | G02F 1/1345 |
| 2012/0274899 | A1 | 11/2012 | Wang et al. | |
| 2015/0206008 | A1 | 7/2015 | Border et al. | |
| 2017/0325675 | A1 | 11/2017 | Liu et al. | |
| 2017/0343822 | A1 * | 11/2017 | Border | G02B 5/3083 |
| 2017/0357879 | A1 | 12/2017 | Odaibo et al. | |
| 2018/0136486 | A1 | 5/2018 | Macnamara et al. | |
| 2019/0065970 | A1 | 2/2019 | Bonutti et al. | |
| 2019/0313895 | A1 | 10/2019 | Hayashi et al. | |
| 2020/0187775 | A1 | 6/2020 | Oh et al. | |
| 2020/0257879 | A1 | 8/2020 | Solanki et al. | |
| 2020/0288963 | A1 | 9/2020 | Lin et al. | |
| 2020/0349710 | A1 | 11/2020 | Paschalakis et al. | |
| 2020/0388383 | A1 | 12/2020 | Lane et al. | |
| 2020/0405148 | A1 | 12/2020 | Tran | |
| 2021/0004957 | A1 * | 1/2021 | Aalamifar | G16H 50/30 |

OTHER PUBLICATIONS

"U.S. Appl. No. 17/664,993, Notice of Allowance mailed Sep. 27, 2022", 8 pgs.

"IExaminer", Welch Allyn, i[Online]. Retrieved from the Internet: <URL: https://www.welchallyn.com/en/microsites/iexaminer.html>, (Accessed Jun. 1, 2022), 3 pgs.

"Nanodropper Adaptor", Nanodropper, Inc., [Online]. Retrieved from the Internet: <URL: https://nanodropper.com/product/nanodropper-adaptor/?gclid=Cj0KCQjwpv2TBhDoARIsALBnVnIYyKr5trtq0tYsM0GcRKRPfe8rm1uMkLanPea0b--bEyLJmYqoBNYaAnEyEALw_wcB>, (Accessed Jun. 1, 2022), 9 pgs.

"Nexy at a Glance", NextSight, [Online]. Retrieved from the Internet: <URL: https://www.nextsight.info/products-solutions/nexy>, (Accessed Jun. 1, 2022), 4 pgs.

"Nexy-Next generation robotic retinal imaging system, optimized for telemedicine and AI applications.", NextSight, [Online]. Retrieved from the Internet: <URL: https://www.nextsight.info/>, (Accessed May 31, 2022), 4 pgs.

"Zeiss Visuscout 100 Handheld Fundus Camera", Zeiss Group, [Online]. Retrieved from the Internet: <URL: https://www.zeiss.com/meditec/int/products/retinal-cameras/visuscout-100-handheld-fundus-camera.html>, (Accessed Jun. 1, 2022), 7 pgs.

Hacisoftaoglu, Recep, et al., "Deep Learning Frameworks for Diabetic Retinopathy Detection using Smartphone-based Retinal Imaging Systems (Thesis)", Department of Computer Science and the Graduate School of University of Central Arkansas, (Dec. 2019), 81 pgs.

Kent, Christopher, "Getting Drops Onto the Eye: Low-tech Solutions", Review of Ophthalmology, [Online]. Retrieved from the Internet: <URL: https://nanodropper.com/product/nanodropper-adaptor/?gclid=Cj0KCQjwpv2TBhDoARIsALBnVnIYyKr5trtq0tYsM0GcRkRPfe8rm1uMkLanPeaob--bEyLJmYqoBNYaAnEyEALw_wcB, (Sep. 12, 2017), 3.

Ramachandran, R, et al., "Automated diabetic retinopathy detection in smartphone-based fundus photography using artificial intelligence", Eye 32. The Royal College of Ophthalmologists. (Mar. 9, 2018), 7 pgs.

U.S. Appl. No. 17/664,993 U.S. Pat. No. 11,564,568, filed May 25, 2022, Eye Imaging System and Fundus Camera Positioning Device.

* cited by examiner

Coronal Plane P2

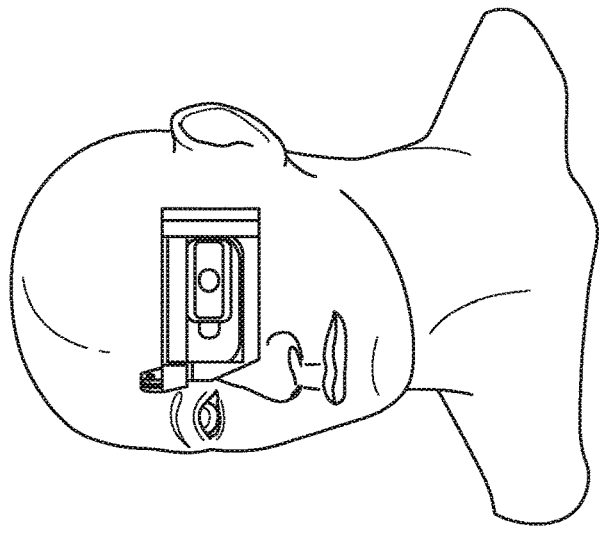
FIG. 7C
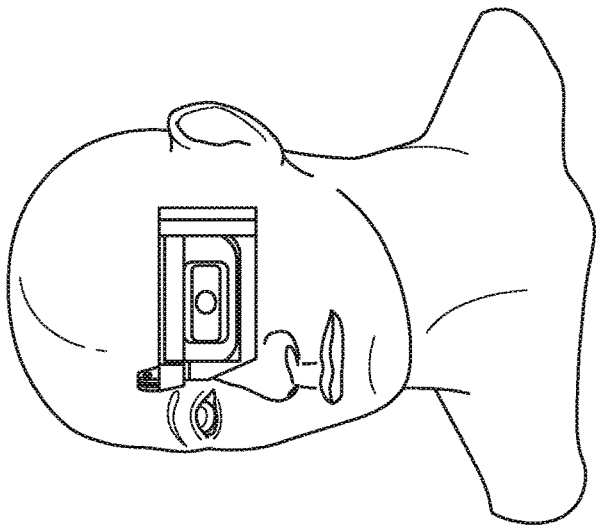
FIG. 7B
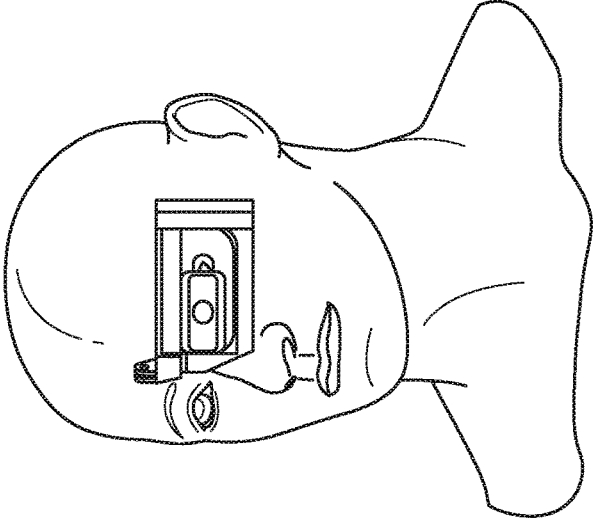
FIG. 7A

Caruncle: Location for Droplet

Eyelid

Caruncle

Upper Panctum
Plio Semilunaris
Superior
Lacrimal Canal

Lacrimal
Sack
Lacrimal
Duct

Inferior
Lacrimal
Canal

Lacrimal
Gland

Lacrimal
Gland Ducts

Eyelashes

Sclera

Iris

Pupil

**Superior Lacrimal
Canal: Location
for Droplet**

**Location for
Droplet**

Lower
Punctum

1002

1004

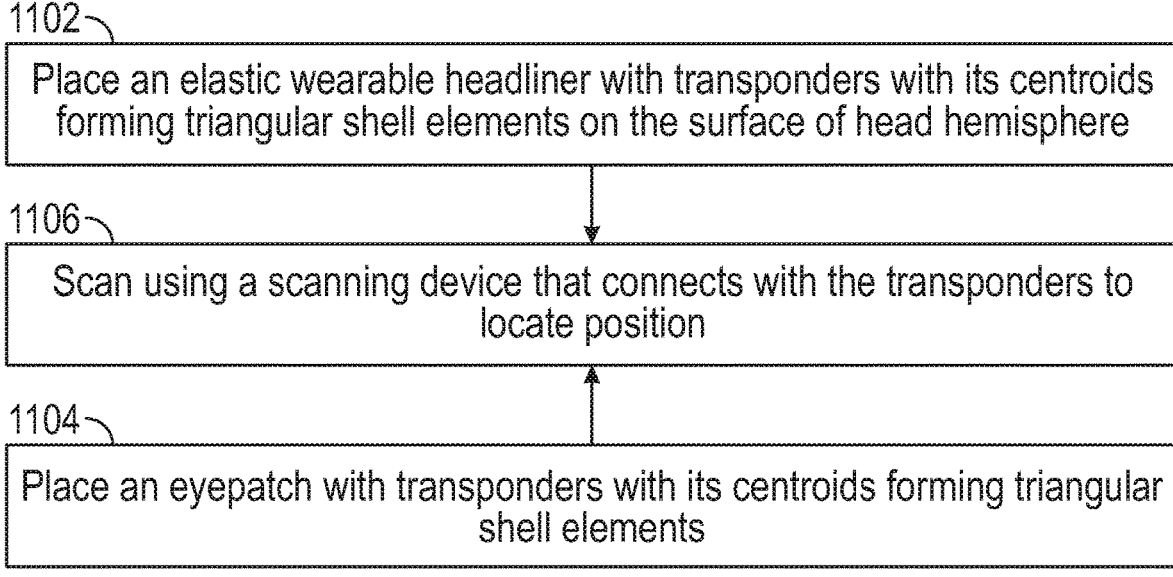

1102
Place an elastic wearable headliner with transponders with its centroids forming triangular shell elements on the surface of head hemisphere 1106
Scan using a scanning device that connects with the transponders to locate position 1104
Place an eyepatch with transponders with its centroids forming triangular shell elements

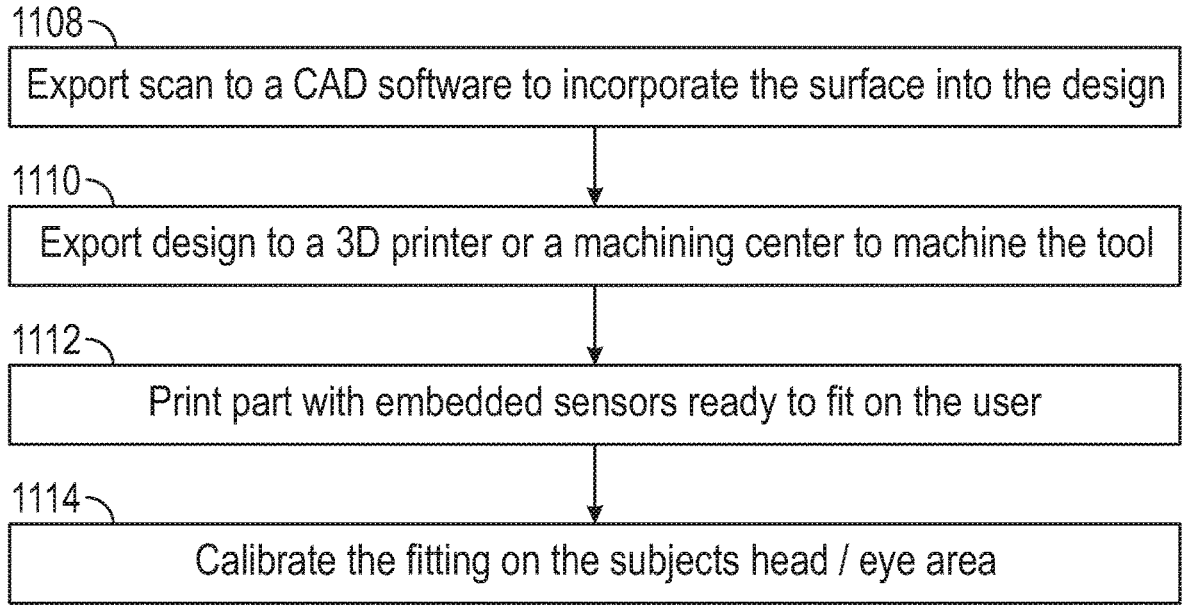

1108
Export scan to a CAD software to incorporate the surface into the design

1110
Export design to a 3D printer or a machining center to machine the tool

1112
Print part with embedded sensors ready to fit on the user

1114
Calibrate the fitting on the subjects head / eye area

FIG. 11

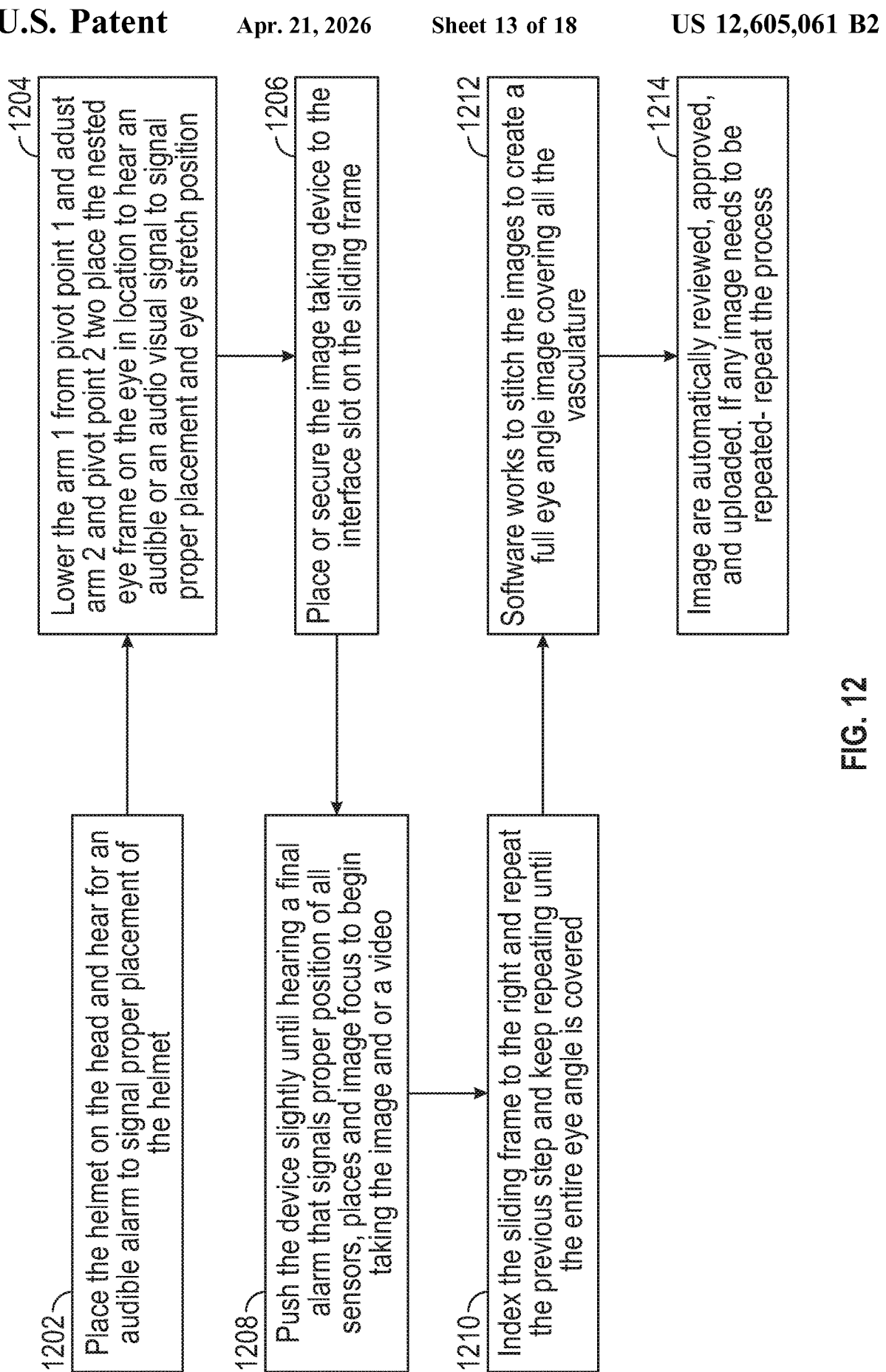

1202 — Place the helmet on the head and hear for an audible alarm to signal proper placement of the helmet 1204 — Lower the arm 1 from pivot point 1 and adjust arm 2 and pivot point 2 two place the nested eye frame on the eye in location to hear an audible or an audio visual signal to signal proper placement and eye stretch position 1206 — Place or secure the image taking device to the interface slot on the sliding frame 1208 — Push the device slightly until hearing a final alarm that signals proper position of all sensors, places and image focus to begin taking the image and or a video 1210 — Index the sliding frame to the right and repeat the previous step and keep repeating until the entire eye angle is covered 1212 — Software works to stitch the images to create a full eye angle image covering all the vasculature 1214 — Image are automatically reviewed, approved, and uploaded. If any image needs to be repeated- repeat the process

FIG. 12

EYE IMAGING SYSTEM AND FUNDUS CAMERA POSITIONING DEVICE

CLAIM OF PRIORITY

This Continuation-In-Part (CIP) patent application claims the benefit of priority of: (1) Shah et al. U.S. patent application Ser. No. 17/664,993, filed on May 25, 2022 entitled "EYE IMAGE SYSTEM AND FUNDUS CAMERA POSITIONING DEVICE;" and (2) U.S. Provisional Patent Application Ser. No. 63/202,045, entitled "EYE IMAGE CAPTURE SYSTEM WITH AI SUPPORTED HEALTH MONITORING AND MANAGEMENT," filed May 25, 2021, each of which is hereby incorporated by reference herein in its entirety.

TECHNICAL FIELD

This document pertains generally, but not by way of limitation, to eye imaging and image analysis for diagnosis, monitoring, or therapy, and more particularly but not by way of limitation to such a system employing trained artificial intelligence and machine learning models and a fundus camera or other eye imager positioning device such as a helmet.

BACKGROUND

Certain diseases can have specific effects on the vasculature in the eyes, which may be possible to detect, such as by an ophthalmologist who is appropriately trained to identify one or more indications of one or more specific diseases, such as using one or more features or patterns observable via specific vasculatures of a human patient or other subject.

SUMMARY

The present inventors have recognized, among other things, that an eye image capture system such as with artificial intelligence (AI) image analysis capability can help support health monitoring and management using eye imaging and videos that can help identify and monitor the presence or states of one or more diseases or physiological conditions of a human patient or other subject. Appropriately configured, such a system can permit techniques that can offer a unique perspective on eye health, body health, or both.

Some illustrative examples of ocular-specific diseases and some potentially life-threatening systemic diseases that can be accompanied by manifestations observable and imageable in the eye can include (but are not limited to) the following: diabetes and diabetic retinopathy, high blood pressure, stroke, glaucoma, sickle cell disease, thyroid disorders, cancer, arthritis, multiple sclerosis, high cholesterol, brain tumors, mild cognitive impairment (MCI), Alzheimer's disease, or concussions.

Each of these diseases or physiological conditions can have specific effects upon the eye, such as upon the vasculature in the eye. Therefore, indications of such specific diseases or physiological conditions are possible to detect, such as by an ophthalmologist who is appropriately trained to identify one or more indications of one or more specific diseases or physiological conditions, such as using one or more visual features or patterns observable via specific vasculatures in the eye.

Using the present techniques, disease or physiological condition detection can include one or more AI-driven techniques, such as can employ a trained Learning Model for image analysis, or other image or pattern recognition techniques, such as for detecting, monitoring, classifying, or diagnosing one or more of the above specific disease or other physiological conditions. Such techniques can be used, for example, to help identify one or more changes in the vasculature or nerve structure associated with the eye. For example, this can include locating such a change in a vascular feature and identifying such a change at the right time. The eye can provide direct non-invasive access to observe the vasculature and nerve structure of the eye. Such visual observations of features within the eye can be captured via an eye imager such as a fundus camera, which can capture still or video retinal images that can be stored, monitored, and analyzed.

However, accurate disease or physiological condition detection using such a system and techniques can be strongly tied to retinal image quality. Retinal image quality is a composite of a number of different factors, such as one or more of: (1) physics-related issues such as one or more of contrast, resolution, noise, signal or noise artifacts, or distortion; (2) one or more grader/evaluator-related or photographer-related issues such as can involve one or more visual perception, training, or experience; (3) one or more task-dependent issues such as can involve one or more of quantitative accuracy, photographic focus discernibility such as can be due to one or more of haze or shadow sensitivity, specificity, or diagnostic accuracy; (4) one or more patient-related issues such as can involve one or more of lens or media shadows, debris in the imaging optical path, smears or opacities on the imaging camera optics, ocular aberration, or retinal pigmentation; or (5) patient positioning, such as can involve the ability to align a fundus camera or other ophthalmoscope device with the eye repeatably without overly relying on a high skill level of the operator.

One general problem to be solved is that, the more accurate an image needed, the more sophisticated the devices that must be used to capture and process the image and, therefore, the more expensive the examination becomes, even with well-trained and experienced ophthalmologists. In an example of an approach, imaging can start with using a handheld fundus camera or a tabletop ophthalmoscope. Among the potential image quality issues mentioned above, the first one, physics-related issues, can benefit from using proper optics and local AI-based software. However, the rest of the above-mentioned image quality issues can potentially benefit greatly from providing a user-friendly system such as can help to reduce, minimize, or completely eliminate the need for human caregiver or diagnostician intervention with the patient in the image-taking process. Some illustrative examples of such a system, such as described in detail below and herein, can also benefit by being one or more of portable, installed at a location, or preferably wearable by the patient and usable without requiring assistance from another individual. As explained herein, portions of the system can be arranged to be capable of positioning the patient and eye repeatably with respect to such portions of the system, or vice-versa. This can include using one or more of AI or other automation assistance or one or more poke yoke type mechanical features.

Specific to the physical alignment of the patient with respect to one or more image capture optics portions of the system, unlike other imaging processes such as MRI or X-Ray, there are not sufficiently robust fixtures available to help align the patient, the patient's eye, or the area of the image of or within the patient's eye to be captured by the fundus camera or other ophthalmoscope. Also, unlike other imaging disciplines, in eye imaging, the target image area is free to move even when the patient is maintained at a fixed or stable position or location—the eye can still move or blink and cannot be held still. In fact, the autonomic response of a human eye is to blink closed when the eye sees an object coming towards it. This is an eye defense mechanism. One approach to help accommodate or compensate for such a defensive reflex can be to help either the patient or a caregiver/operator holding the eye open, such as using two fingers (or other mechanical stretching features) for stretching the skin above and below the eye, and then compressing a bellows-type or other appropriate attachment onto the area about the eye, such as to help manage the focal length of the optics of the fundus camera or other ophthalmoscope to help obtain an appropriate focus. Then, based on one or more aspects of what is seen on an imaging display screen, a picture can be captured and stored. This is an inefficient process that can yield up to 30% of images captured being non-gradable by an evaluating diagnostician.

Certain approaches can be further limited because a diagnosis is based on a "snapshot" in time (e.g., one or more images taken during a single physician visit) or a few images captured years apart, at best. Additionally, this limited dataset may be stored in the data silos of the individual ophthalmology clinics at which such images were obtained. The present inventors have also recognized, among other things, that to be effective at diagnostic or health monitoring, such images should be obtained much more frequently, such as can help to catch the onset of a particular disease early on via observable anomalies in the eye image. Furthermore, the images of or within the eye should be analyzed using one or more trained statistical Learning Models or other statistical methods that can be capable of detecting minor changes in the anatomy such as can be indicative of a disease-induced pathology.

Notably, approximately 50% of diabetic patients do not go to an ophthalmologist for an annual eye exam in the U.S.A. This results in a higher cost of associated physiological disease conditions (e.g., diabetic retinopathy), such as can be due to late detection of worsening conditions in the diabetic patient. This percentage drops even lower among diabetic patients visiting ophthalmologists in developing and emerging countries, such as to 20-30%.

The present inventors have recognized, among other things, the benefit of providing a system that can be capable of being used at any location, or otherwise helping permit a patient or other subject to take his or her own image of or within the eye, such as with sufficiently high image quality and repeatability to have useful diagnostic value for one or more various specific eye or systemic disease conditions. Such independently-acquired images can optionally be stored at a location that is owned or controlled by the subject, which can provide the subject the ability to do with such images as they please. In such a subject-controlled eye image data environment, the subject can provide or control access, as desired, to one or more of: one or more doctors, to one or more healthcare providers or payers, or to the research community, such as to receive a diagnosis, treatment planning, or even remuneration, whichever is appropriate. This document discloses illustrative examples of portions of such an image capture system and supporting ecosystem such as can help accomplish or empower individual health management. This type of system can be sold or provided under a franchise-type model, such as in which one or more rural/suburban/urban clinics can be set up on such as on a pay-per-use or a pay-per-system business model.

This document proposes an easier and more cost-effective system for an eye examination, such as which is capable of being used in a primary care setting by a primary care nurse or doctor, or in an urgent care setting, or even at a standalone kiosk or for self-examination at home, such as to screen a patient for potential further analysis, such as by a remote panel of doctors in a proprietary or other health management ecosystem, such as for specific referral to an ophthalmologist for further detailed exam or diagnosis. The present systems and techniques can include one or more versions that can help provide direct feedback to the patient or other user with low latency and high clarity, such as to help enable action to be taken by a primary care nurse or doctor or even by the patient.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7A (stage left), FIG. 7B (stage middle), and FIG. 7C (stage right) illustrate an example of various positions of the indexing fundus camera movement stage.

FIG. 11 is a flow chart illustrating generally an example of a process of forming the conformal components used in the helmet system.

FIG. 12 is a flow chart illustrating generally an example of a process for eye image capture.

DETAILED DESCRIPTION

This document describes systems and methods for eye imaging and image analysis for diagnosis, monitoring, or therapy, and more particularly but not by way of limitation to such a system employing trained artificial intelligence and machine learning models and a fundus camera positioning device such as a helmet, which can help improve the positioning and repeatability of a fundus camera or other ophthalmoscope with respect to the eye, such as can help provide more accurate eye images for capture, monitoring, analysis, or diagnosis. More particularly, this document describes, among other things, an eye imaging system, comprising a head-wearable fundus camera positioning helmet. In this document, the term "helmet" is used herein to refer to any head-wearable fixture device, such as a hat, head-band, head-ring, head-brace, crown, headpiece, or any other wearable head-fixture. In an example, the helmet can include a patient-specific conformable interior head liner that can be customized or otherwise arranged to fit about a head of a specific patient. The head liner can include head location fiducials defining a specified plane with respect to a transverse plane of the head of the specific patient. The helmet can also include an outer shell. An articulating fundus camera fixture can be attached to the outer shell of the helmet. The fixture can include a fundus camera positioning indexing system such as to indicate position information about a position of the fundus camera with respect to an eye of the patient for acquiring one or more fundus camera images at the indicated position such that fundus camera images recorded over a chronic period of time can be assessed using the corresponding position information from the fundus camera positioning indexing system.

Figure 1B:
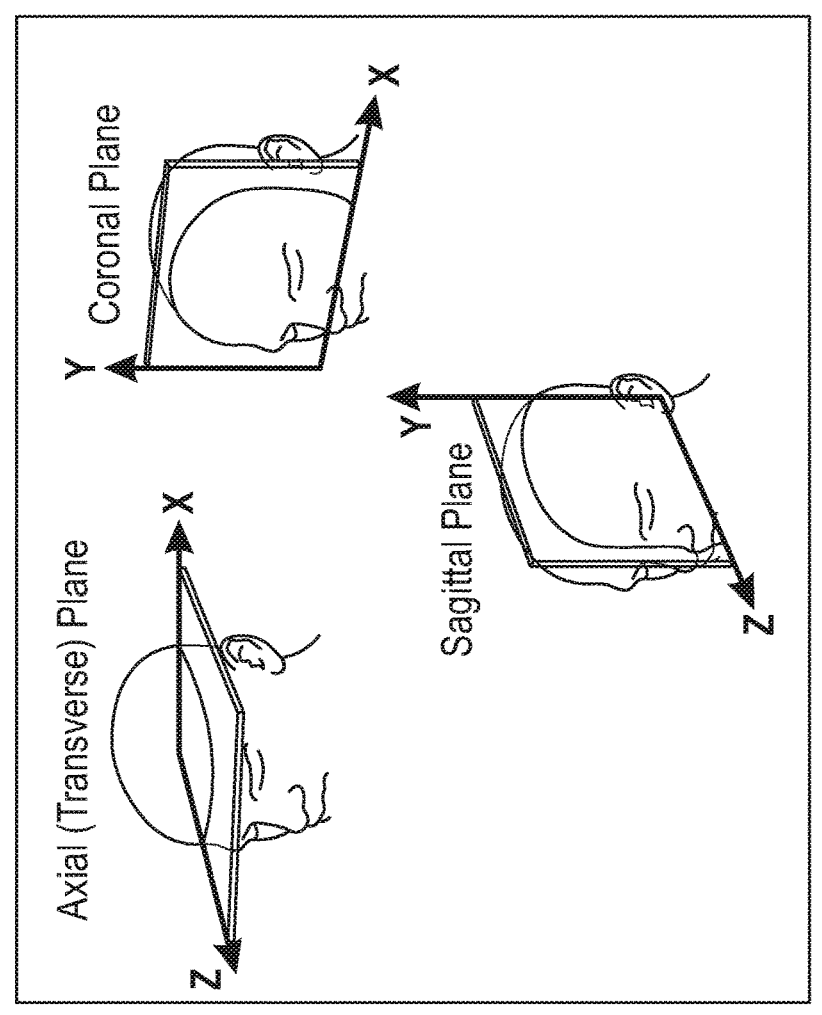
FIG. 1B shows these same three mutually orthogonal planes with respect to an oblique perspective view of a head of a human subject.
Figure 1A:
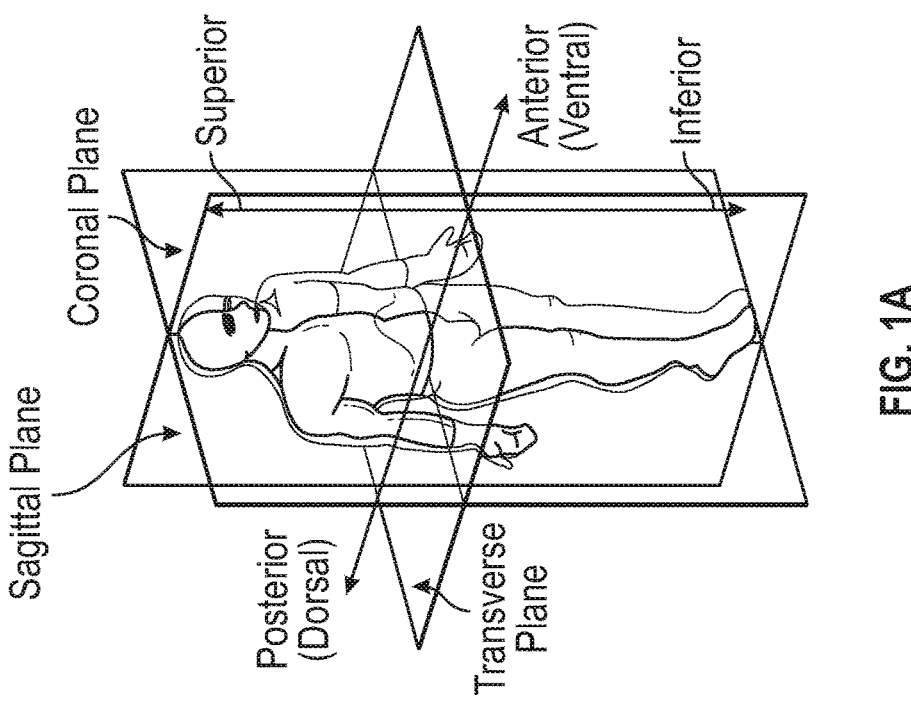
FIG. 1A is an illustration of anatomic reference planes defined for use with a human body of a standing human subject.

FIG. 1A is an illustration of anatomic reference planes defined for use with a human body of a standing human subject, with the subject's head oriented in a superior direction and the subject's feet oriented in an inferior direction. In this patient orientation, three mutually orthogonal reference planes are shown: a transverse plane (also referred to as an axial plane), a sagittal plane, and a coronal plane.

FIG. 1B shows these same three mutually orthogonal planes with respect to an oblique perspective view of a head of a human subject. FIG. 1B also shows "x" and "y" directions with respect to the transverse plane, the coronal plane, and the sagittal plane.

Figure 2:
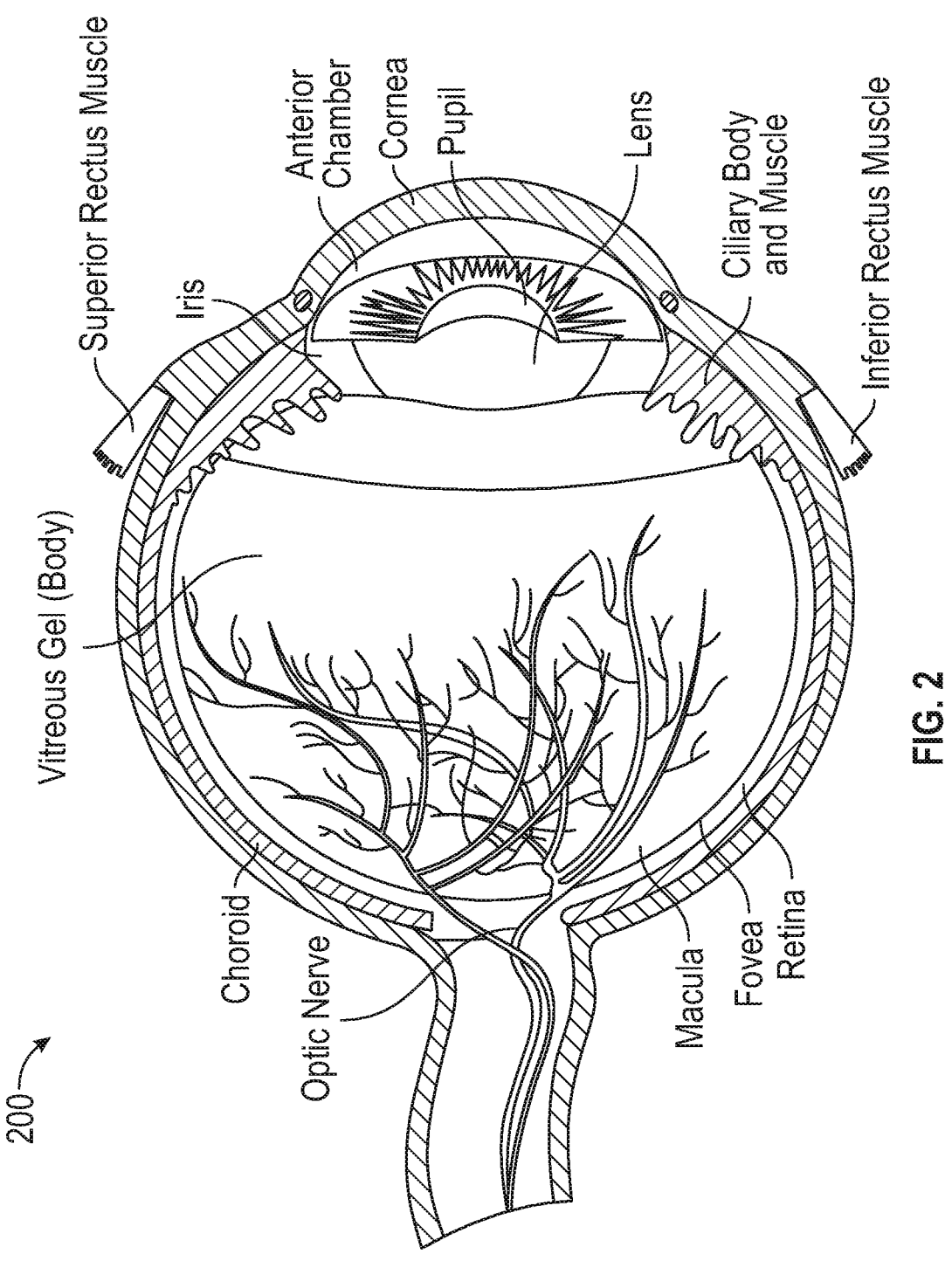
FIG. 2 shows an illustrative side cross-sectional view illustrating an example of anatomy of a human eye.

FIG. 2 shows an illustrative side cross-sectional view illustrating an example of anatomy of a human eye 200, including a cornea, anterior chamber, pupil, lens, iris, ciliary body and muscle, superior and inferior rectus muscles, vitreous gel (body) within the eye globe, a choroid, an optic nerve, a macula, a fovea, and a retina. Images captured of the interior of the patient's eye 200 will be referred to as retinal images, even though other intraocular structures may be present in such internal images of the eye 200.

Figures 3A, 3B:
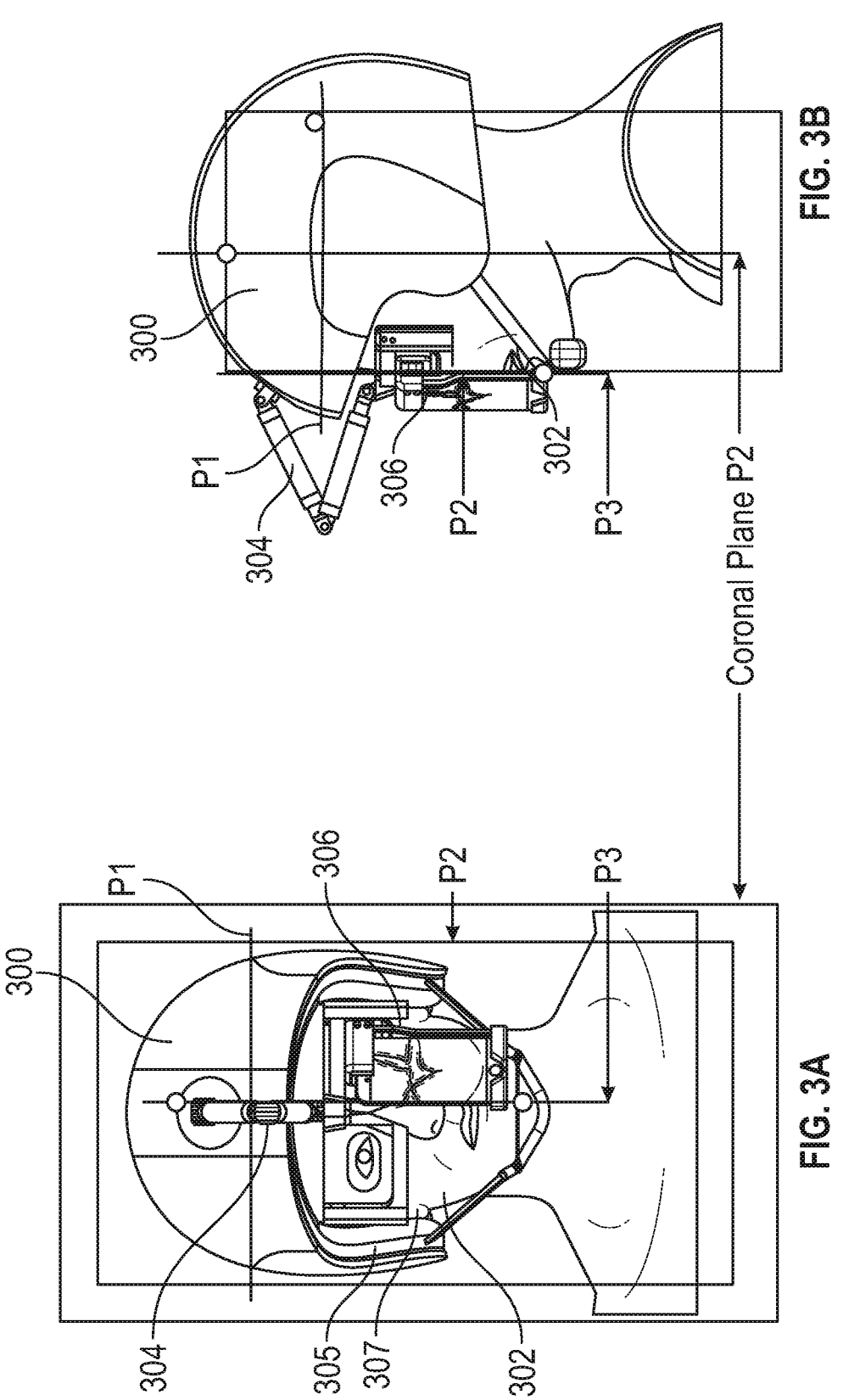
FIG. 3A (front view) and FIG. 3B (side view) shows an illustrative example of a head-worn fixture, such as a helmet.

FIG. 3A (front view) and FIG. 3B (side view) shows an illustrative example of a head-worn fixture, such as a helmet 300 being worn upon a human patient's head 302. The helmet 300 can include a chin strap or chin strap assembly, such as to secure the helmet 300 to the patient's head in a particular position and orientation, and to inhibit sliding or other movement of the helmet 300 on the patient's head after the chin strap has been snugly secured. The chin strap assembly can optionally include one or more sensors. For example, the one or more sensors can include one or more position sensors, pressure sensors, or strain gauges, such as which can be used to provide sensor information that can be signal-processed and used to confirm proper helmet placement and positioning on a subject's head. Strain gauges can be mounted onto or incorporated into the textile or elastomeric chin strap, and such sensors can be used to provide a numerical value of strain or stress corresponding to the stretched distance of the chin strap being used to keep the helmet snug to the head at the desired orientation of the reference planes defined by the fiducial markers or other positioning devices included in the helmet. For example, elastic stretch sensors and strain gauges are available from LEAP Technology, Bjerndrup Bygade 23, 6200 Aabenraa, Denmark (www.leaptechnology.com).

When worn, the helmet defines a plane P1, parallel to the transverse plane, formed by the contact or interface points in P1 at the three farthest points from each other on the head 302. These three farthest points from each other on the patient's head 302 can correspond to contact fiducials on the helmet 300, with such contact fiducials being located on the helmet 300 so as to make contact with these three farthest points from each other on the head 302. The helmet 300 can include an articulating fundus camera (or other eye imager) fixture 304, which can be mounted to an outer shell 305 of the helmet 300, and which can position a fundus camera (or other eye imager) mount 306 in a defined plane P2 that is parallel to the coronal plane of the patient's head 302. The helmet 300 can also include an a patient-specific conformable interior head liner 307, which can be customized to fit about a head of a specific patient. In an example, the head liner 307 can include the head location fiducials defining the specified plane P1 with respect to a transverse plane of the head of the specific patient.

In FIGS. 3A-3B, P1 is a plane formed by the contact or interface points at the three farthest points on the human head 302 and the contact fiducials on the helmet 300. P1 is parallel to the transverse plane shown in FIGS. 1A-1B, such as within an acceptable orientation tolerance for eye imaging, which can be defined by indexing sensors that can be included in the articulating fundus camera fixture 304, in the fundus camera mount 306, or elsewhere. Plane P2 is a plane that can be formed by the contact or interface points or surfaces of the fundus camera mount 306, such as when the fundus camera mount 306 is placed against the bone structure surrounding the eye 200. The plane P2 can be parallel to the coronal plane shown in FIGS. 1A-1B, such as within an acceptable orientation tolerance for eye imaging, which can be defined by indexing sensors that can be included in the articulating fundus camera fixture 304, in the fundus camera mount 306, or elsewhere. The planes P1 and P2 can be formed essentially parallel to the standard human planes shown in FIGS. 1A-1B, so that the helmet 300 can be used to create its own coordinate system, which can represent a subset of an overall human coordinate system.

The fundus camera mount 306 can include a custom-formed eyepiece, such as can be tailored in shape to fit against the bone structure surrounding the eye 200 of a particular patient, such as from an impression made of the patient's bone structure. The custom formed eyepiece on the patient-facing side of the fundus camera mount 306 can be created by taking putty impressions using a shape-formable mold, such as in a similar manner used for forming dental impressions. After the mold has been shaped-formed against the bony structure about the eye 200 of the particular patient, the resulting mold can be image-scanned. The image-scan data can be imported to three-dimensional (3D) printer. The 3D printer can be used to print a customized patient-specific conformable interior eye region liner customized to fit about an eye 200 of the specific patient, such as which can be attached to a patient-facing side of the fundus camera mount 306, so that it can be seated securely against the mating portions of the bony structure about the eye 200 of the particular patient.

Figure 4B:
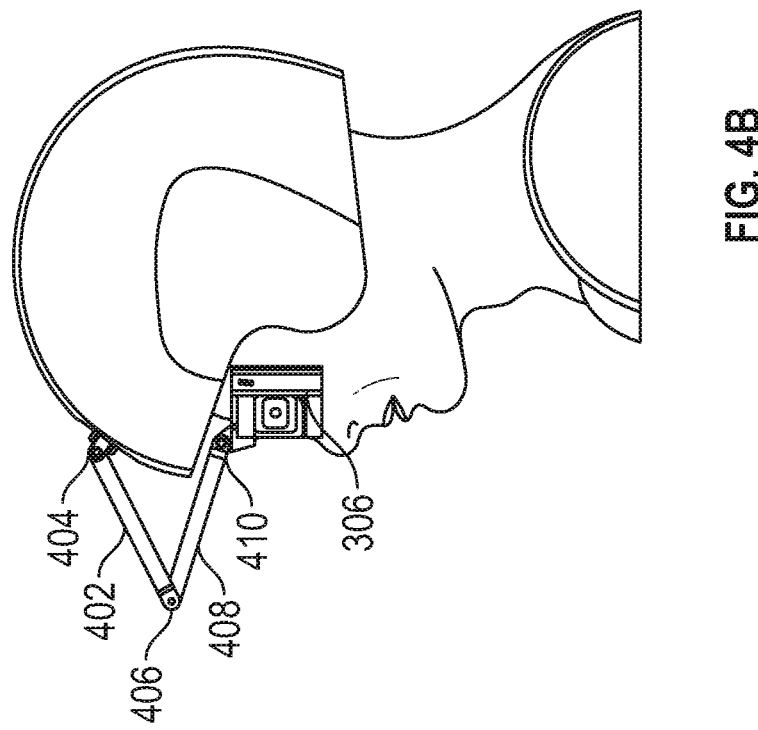
FIG. 4A (front view) and FIG. 4B (side view) shows an illustrative example of the helmet with additional details of the helmet.
Figure 4A:
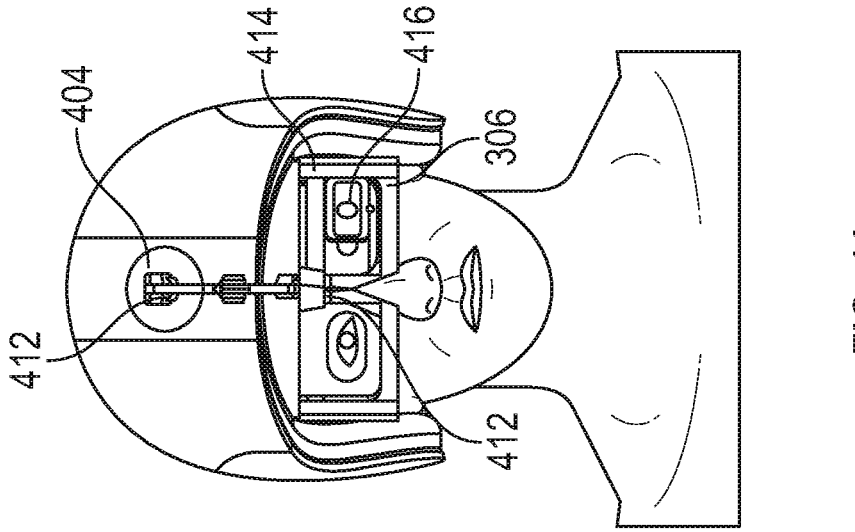

FIG. 4A (front view) and FIG. 4B (side view) shows an illustrative example of the helmet 300 with additional details of the helmet 300, such as additional details with respect to the articulating fundus camera fixture 304 and the fundus camera mount 306. The articulating fundus camera fixture 304 can provide an articulating arm including a first arm member 402 extending between (1) a first pivot point 404 mounted via an attachment extension to the outer shell 305 of the helmet 300 and (2) a second pivot point 406. A second arm member 408 can extend between the second pivot point 406 and a third pivot point 410. The fundus camera mount 306 can extend from the third pivot point 410 and can be oriented in plane P2 to be parallel to the coronal plane, such as by pressing the 3D-printed customized physical part so that it can be seated securely against the mating portions of the bony structure about the eye 200 of the particular patient. The number of arm members or pivots (or both) can be changed, for example, increased in number to provide increased ease of adjustment.

The fundus camera mount 306 can include an image capture assembly, to which a fundus camera can be mounted, for one or both of the left or right eye 200 of the patient. The articulating fundus camera fixture 304 and head-wearable or other wearable fixtures like the helmet 300 can include one or more micromotors, one or more accelerometers, gyroscopes, or other indexing position sensors, or both, such as described further herein. This can help to provide positioning information that can be used for at least one of accurately positioning a fundus camera or other ophthalmoscope, accurately recording a position of the fundus camera or one or more components of the articulating fundus camera fixture 304, the fundus camera mount 306, or both. Illustrative examples of possible gyroscope locations 412 are shown in FIGS. 4A and 4B. An illustrative example of a possible micromotor location 414 is also shown in FIG. 4A. A micromotor can be included at the micromotor location 414 such as to move an indexing fundus camera movement stage 416 configuring for carrying a fundus camera or other imaging or measurement device mounted thereto.

The indexing fundus camera movement stage 416 can be coupled to the fundus camera mount 306 or to the patient-conformable eye region liner. The indexing fundus camera movement stage 416 can be translatable or otherwise movably positionable, such as in or between one or multiple planes, such as shown in FIG. 5C (e.g., translatable up and down in a plane, translatable left and right in a plane, movable in a yaw direction at a specified distance from a specified point on a specified plane that is parallel to the coronal plane of the patient, or any combination of these) with respect to the patient eye 200. Such translation or other movement of the fundus camera movement stage 416 can be in a direction that is generally parallel to the coronal plane of the head of the specific patient, or can include semi-spherical "yaw" motion looking toward the center of a pupil of the eye 200 or other selected point on a plane that is parallel to the coronal plane. The indexing fundus camera movement stage 416 can be configured to carry the fundus camera or other ophthalmoscope device. The indexing fundus camera movement stage 416 can include a indexing position sensor, such as which can be configured to indicate position information about a position of the fundus camera in the direction generally parallel to the coronal plane of the head of the specific patient as part of the position information being provided from the helmet-worn fundus camera positioning indexing system.

In FIGS. 3A, 3B, 4A, and 4B, the helmet 300 can include the outer shell 305 and the inner liner 307. The outer shell 305 of the helmet 300 can be made of a hard material, such as which can withstand normal impacts, such as of the type that can be use for sports, or safety, or in general for protecting the patient's head. The internal liner 307 can be conformal to the head of the particular human patient wearing the helmet 300. The internal liner 307 can be a patient-specific liner 307. A patient-specific liner 307 can be created by pre-scanning the patient's head 302. Based on the scanning information, a 3D-printed liner 307 can be created. The printed liner 307 can be formed to include protruded fiducials that protrude toward the patient's head 302. The protruded fiducials can be located at the three farthest points from each other on the patient's head 302. Such protruding fiducials can serve to define contact locations between the helmet 300 and the patient's head 302.

The articulating fundus camera fixture 304 can include a plurality of pivot points, such as 3 or more pivot points. The articulating fundus camera fixture 304 can include an attachment location on the outer shell 305 of the helmet 300, such as to connect the articulating fundus camera fixture 304 to the outer shell 305 of the helmet 300 at (1) a specified location in the plane P1, which can be parallel to the transverse plane of the patient, as described, and at (2) a specified location in the plane P2, which can be located parallel to the coronal plane of the patient, and at (3) a specified location in the sagittal plane of the patient.

The articulating fundus camera fixture 304 can include an attachment location on the outer shell 305 of the helmet 300 at or near which the first pivot point 404 can be located, from which the first arm member 402 can extend, such as to serve as a lever arm. The first pivot point 404 can allow for a vertical motion for the first arm member 402, such as can help orient or position or place the fundus camera mount 306 against the bony structures about each of the patient's left and right eyes 200. The first arm member 402 can be connected to the second arm member 408 at the second pivot point 406. This allows for vertical up-and-down movement of the first arm member 402 and the second arm member 408, along with the attached fundus camera mount 306 extending from the third pivot point 410 at the distal end of the second arm member 408. This permits positioning and placement of the fundus camera mount 306 at a desired location in relation to the coronal plane of the patient. The second pivot point 406 allows for the second arm member 408 to be adjusted to align the fundus camera mount 306 and its image capture assembly to the patient's eye 200 within a plane parallel to the coronal plane of the patient. The second arm member 408 includes the second pivot point second pivot point 406 and the third pivot point 410 at its opposing ends, such as to allow full freedom of alignment motion of the fundus camera mount 306 and its image capture assembly within the sagittal plane, such as to a location in the plane P2 parallel to the coronal plane of the patient. The third pivot point 410 attaches the second arm member 408 to the fundus camera mount 306 and its associated image capture assembly, and allows for the fundus camera mount 306 to be adjusted within the plane P2 parallel to the coronal plane of the patient.

Gyroscopes can respectively be located at possible gyroscope locations 412. In an example, the helmet 300 system can include at least two gyroscopes. A first gyroscope can be located at or near the first pivot point 404 on the outer shell 305 of the helmet 300 and can help maintain the parallel orientation of the plane P1 to the transverse plane of the patient. A second gyroscope can be located on the fundus camera mount 306 and can help maintain the parallel orientation of the plane P2 to the coronal plane of the patient.

A micromotor can be attached at possible micromotor location 414, near the image capture assembly of the fundus camera mount 306. The micromotor can be actuated to translate a indexing fundus camera movement stage 416 carrying a fundus camera such as laterally (from left-to-right or vice-versa) with respect to the left or right eye 200 of the patient. Position information about the indexing fundus camera movement stage 416 can be captured via a digital encoder, and such position information and be stored together with images that are acquired by the fundus camera at the various locations of the indexing fundus camera movement stage 416.

Other position or other sensors can also be included in the helmet 300 system. For example, the internal liner 307 of the helmet 300 can include one or more embedded or attached pressure or other sensors. Similarly, the fundus camera mount 306 can include embedded or attached sensors. The various sensors can form a network of sensors with wired or wireless communication capability, so that such sensors can communicate position or other information to a microcontroller, such as which can be included in the helmet 300 system or communicatively coupled thereto. Such acquired sensor information can be used for positioning the helmet 300 or the various components such as the articulating fundus camera fixture 304 or fundus camera mount 306 or both. Such acquired sensor information can also be stored together with images acquired by a fundus camera carried by the fundus camera mount 306, such as for use in training a Learning Model, or for applying a trained Learning Model for image analysis. For using the sensors for providing positioning assistance to the patient or other user, once image capture readiness conditions are reached, an alarm or alert can be used to notify the patient of the image capture readiness. Such alarm or alert can include an audible or audiovisual alarm, such as can provide an audible beep, a blinking light, or both, or a haptic alert can be provided to the patient to notify the patient of the image capture readiness conditions, so that the image capture process can begin.

Figure 5B:
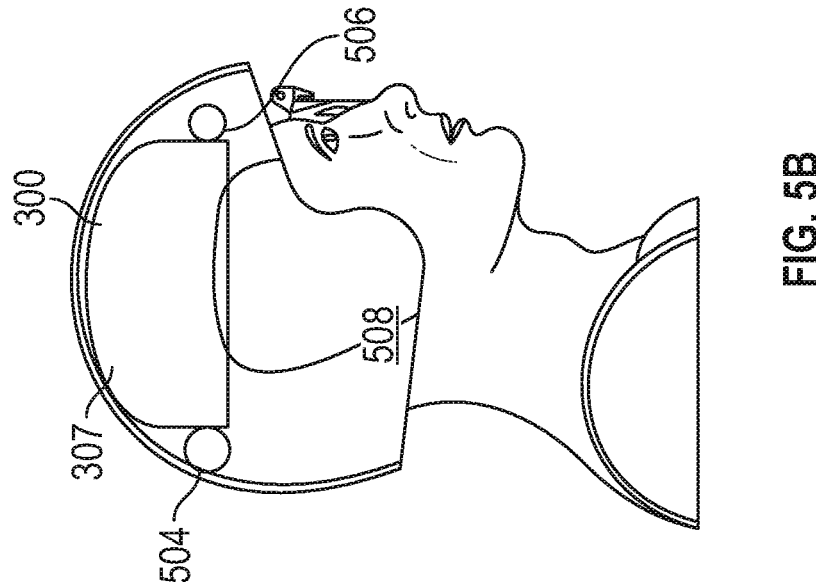
FIG. 5A (front view) and FIG. 5B (side view) shows an illustrative example of the helmet with additional details of the helmet, such as additional details with respect to interlocks and sensors.
FIG. 5C illustrates examples of orientation and movement of a stage for either (or both) of translation or yawing movement.
Figure 5A:
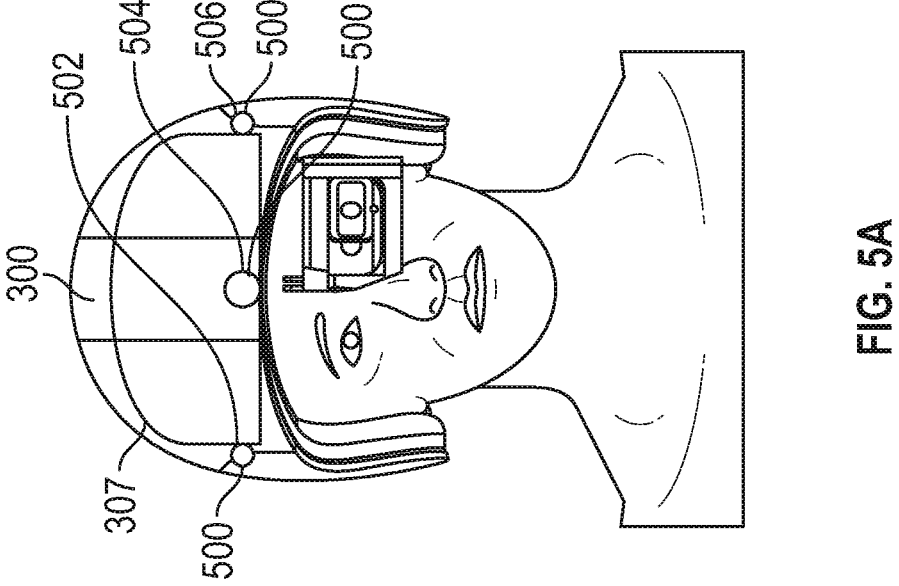
Figure 5C:
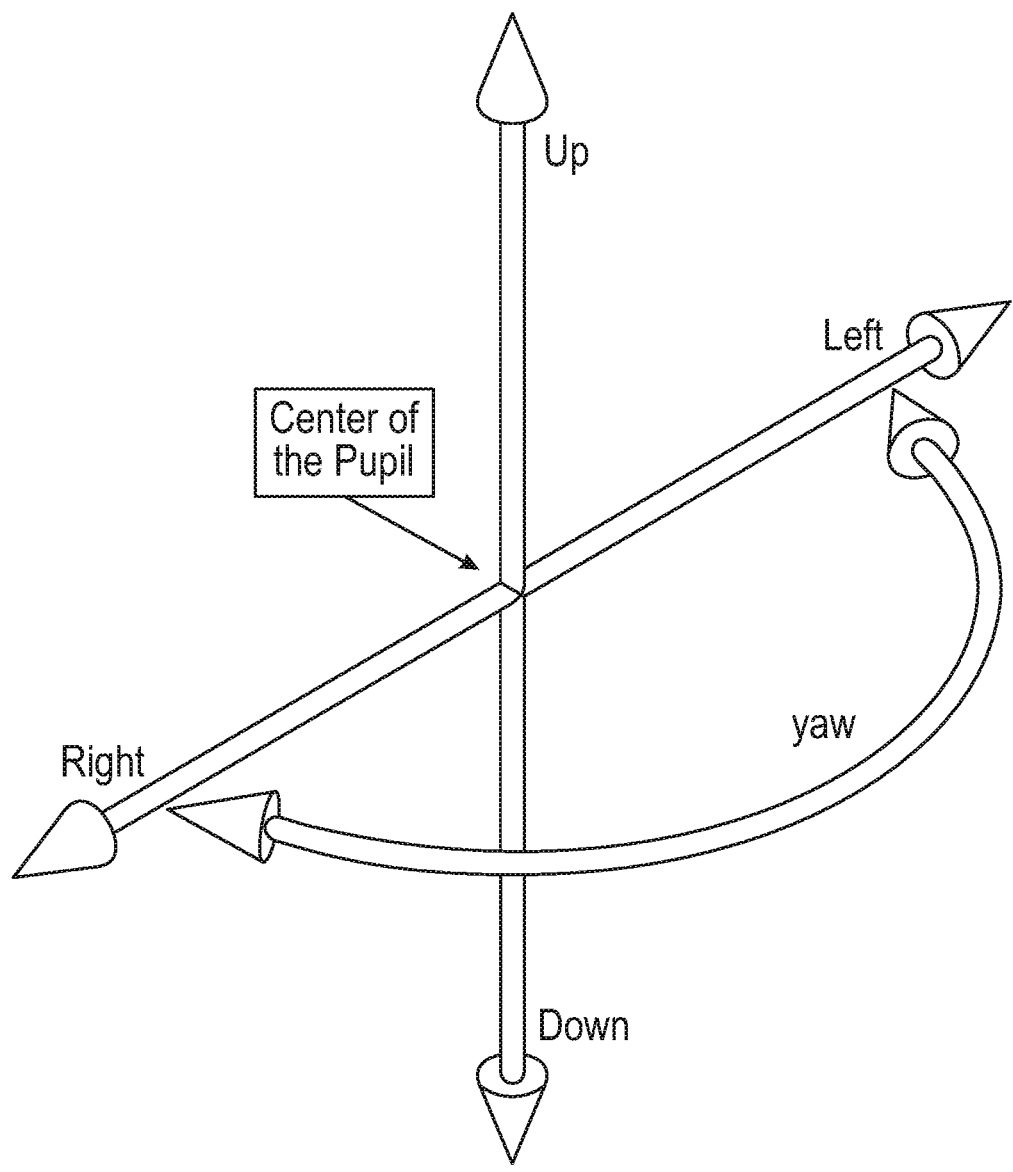

FIG. 5A (front view) and FIG. 5B (side view) shows an illustrative example of the helmet 300 with additional details of the helmet 300, such as additional details with respect to interlocks and sensors 500. For example, the sensors in the helmet 300 system can include a temporal sensor right 502 (TSR) sensor, such as can be located in the internal liner 307 of the helmet 300 near the right temporal side region of the patient's head. An occipital sensor 504 (OS) sensor can be located in the internal liner 307 toward the rear of the helmet 300, near an occipital region of the patient's head. A temporal left sensor 506 (TLS) sensor can be located in the internal liner 307 of the helmet 300 near the left temporal side region of the patient's head. The internal liner 307 of the helmet 300 can also include controller circuitry 508, such as which can include control electronics for the micromotor or other components, memory circuitry, signal processing circuitry, and communication circuitry for wired or wireless communication with the various sensors 500 or for wired or wireless communication with a local or remote external user interface device, which, in turn, can be communicatively coupled to a cloud-based central server computing device.

In FIGS. 3A, 3B, 4A, 4B, 5A, and 5B, the internal liner 307 of the helmet 300 can include or be made from a thermoplastic or a thermoset elastomeric material. For example, the internal liner 307 can include a material ranging in hardness from a Shore 50 through a Shore 90, such as can be measured by a durometer, or a hardness gradient in this range along the hemisphere of the patient's head, or of an appropriate hardness to comply with any local or global regulatory requirements for skin contact by a internal liner 307 of a helmet 300. The internal liner 307 can be formed by an appropriate molding or hand-forming or 3D-printing process. The internal liner 307 can optionally be formed to be chemically or physically foamed, such as to establish or vary the durometer harness, the feel of the material of the internal liner 307, or both. In an example, the internal liner 307 can be made with a printed or molded lattice (see, e.g., https://www.fastradius.com/resources/3d-lattice-design-elements/). Such use of a lattice material for the internal liner 307 can concurrently allow for impact resistance and breathability, which can help enable use of the helmet 300 as a multi-use helmet 300. The internal liner 307 can be conformal and can optionally be customized to the morphology of the particular patient's head, such as described herein. The internal liner 307 can be a monolithic internal liner 307. Alternatively, the internal liner 307 can include multiple inflatable, foam, or other cushions or other pieces, such as which can be individually installed or removed by the end-user to provide a multi-piece internal liner 307. For example, one or more of the individual liner pieces can include a sensor, a fiducial marker or other location feature, or other componentry.

The helmet 300 can be custom fitted with elastomeric spherical or donut-shaped liner elements, such as individually encapsulating or surrounding a sensor such as a ball-bearing structure. Each liner element can be formed from a photo-activated, heat-activated, or pressure-activated cross-linkable polymeric material. The elements of such cross-linkable polymer can be located at 3 locations in the helmet 300, such as explained herein. Two of these can include temporal locations, and the third of these can include an occipital location. The helmet 300 can include a right temporal ball, a left temporal ball, and an occipital temporal ball. The cross-linkable material in these balls can be activated either with the light from an LED source, or heat from a low voltage heater filament or just the pressure activated from the push of the helmet on the person when the helmet 300 is put on the person's head. The liner elements can be mounted onto a flexible cantilever part of the helmet liner such as can help allow deflection as the helmet 300 is pressed onto the head. The wearer can determine a comfortable amount of pressure and press a button to activate the crosslinking process (such as by activating ultraviolet (UV) light) and render the elastic elements rigid, i.e., limiting the flow in any direction. This allows for repeatable placement of the helmet on the head. A helmet 300 placed in any other orientation will fail to activate the sensor network hence the user will not be able to move forward with the measurement process.

The helmet 300 can include or use or can be configured as an Augmented Reality/Virtual Reality (AR/VR) helmet, such as can include one or more of an AR/VR visual display, wireless or wired communication capability, local or remote data logging capability, or one or more other AR/VR features. For data logging, the data can be formatted in any of a number of ways, for example, in a bitmap, in a JPEG file, in a MOV file, as electrical signal data (e.g., voltage amplitude) such as from a sensor or other componentry included within the helmet 300, or in a relational-database compatible format, among other things.

The sensors 500 can be embedded into the internal liner 307 of the helmet 300, such as at the three farthest possible locations from each other in the perimeter of the particular patient's head. In this way, the sensors 500 can form a triangle defining the plane P1 parallel to the transverse plane of the patient. The sensors 500 can include one or more of a strain gauge, a pressure sensor, a force sensor, a limit switch, or a combination of these or other types of sensors 500. The sensors 500 can provide fiducials that can be formed into the internal liner 307 of the helmet 300 at the head-helmet interface points forming the plane P1 parallel to the transverse plane of the patient.

The protruded fiducials can be located at the three farthest points from each other on the patient's head 302. Such protruding fiducials can serve to define contact locations between the helmet 300 and the patient's head 302. The protruded fiducials can be used as sensor placement location to establish a coordinate system custom for every user in reference to all three anatomic reference planes. Sensor insert locations can be determined through head scan or physical measurements. This can help provide repeatable fixture placement that can be used for image processing over multiple measurements for duration of time where sensor measurement data will be compared to original data set collected during initial placement. The same data can be created using different sensor sets as gyroscopes. Sensor inserts can be adaptive to any user helmet with an existing liner and can be located in the liner or in a chin strap of the helmet to help optimize repeatable fixture placement.

The sensors 500 can include one or more gyroscope or accelerometer sensors 500. Such gyroscope or accelerometer sensors 500 can be networked or otherwise communicatively coupled with the other sensors 500, such as position, pressure, or force, sensors, all of which can be wired or wirelessly communicatively coupled to communications circuitry of controller circuitry that can also include signal processing circuitry and memory circuitry for storing and processing the information from the sensors 500. The one or more of the gyroscope or accelerometer sensors 500 can help confirm the positioning or planarity or orientation of the helmet 300 and the fundus camera mount 306 and the indexing fundus camera movement stage 416 or other portions or components of the helmet 300 system. The gyroscopes, accelerometers, or other sensors 500 can be used to collect data when the helmet 300 is in use, such as during image collection, or during other activities, such as can include (but not limited to) sports, driving, armed forces combat or war deployment, daily exercises, activities of daily living, or premature or other infant monitoring, as illustrative examples. The data from the sensors 500 can be used to train or use a Learning Model or to help find an assignable cause to any anomalies that may be measured during eye image acquisition or positioning of the helmet 300 or during other use of the helmet 300, such as in other activities, such as described herein. Such anomalies can be measured in response to an anomaly-inducing event, such as an impact or unnatural acceleration force ("G-force") to the patient's head. For example, when an impact meeting at least one criterion (e.g., an impact exceeding a threshold impact energy or acceleration value) is detected, that information can be used to disregard or otherwise qualify any eye imaging data, eye imager positioning information, or both, obtained within a specified time period after the impact event is detected.

Figure 6B:
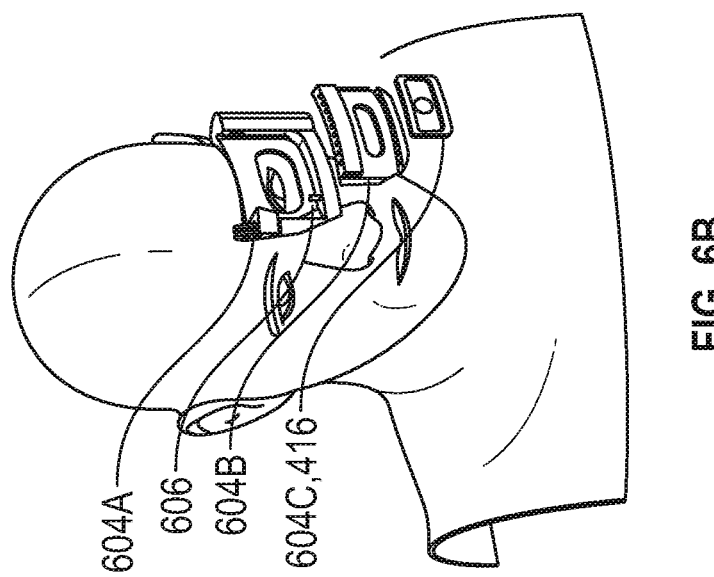
FIG. 6A (assembled view) and FIG. 6B (exploded view) show details of one side (e.g., left eye or right eye) of the fundus camera mount and its various nested or otherwise assembled components.
Figure 6A:
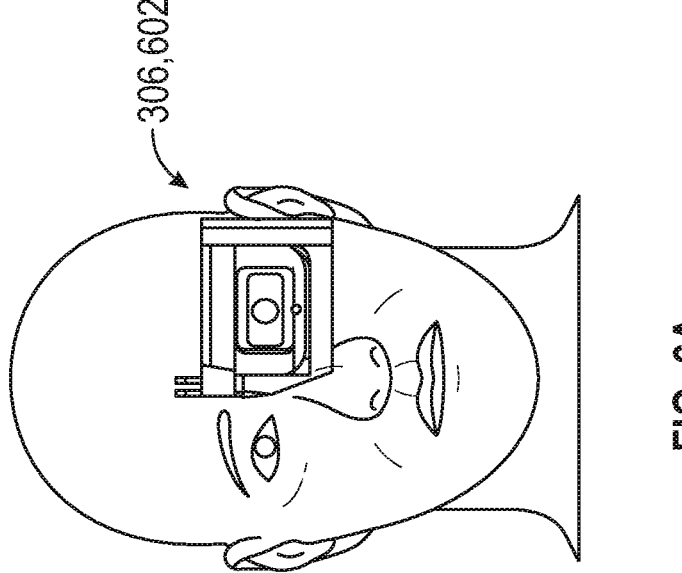

FIG. 6A (assembled view) and FIG. 6B (exploded view) show details of one side (e.g., left eye 200 or right eye 200) of the fundus camera mount 306 and its various nested or otherwise assembled components, such as which can include an image-capture assembly 602 having nested or otherwise coupled assembled components such as frames 604. The fundus camera mount 306 can also include a patient user-interface output indicator 606. The patient user-interface output indicator 606 can include one or more of a positioning indicator, a camera-acquisition "in use" indicator, a patient focus-assist indicator, or the like.

In FIG. 6B, the fundus camera mount 306 or image-capture assembly 602 can include an eye region interface frame 604A. The eye region interface frame 604A can include a surface facing the patient's eye 200, and conforming to and touching the bony region around the patient's eye 200. As explained herein, such a conformable surface can be custom-manufactured, such as by scanning either an impression of the bony region about the patient's eye 200 or directly scanning such region and exporting the scanning such data to a molding or mold-making or 3D-printing device that can replicate the scan data into a customized shape conformable surface that can snugly mate with and against the corresponding bony region about the patient's eye 200. This conformal piece can attach to a patient-facing side of the eye region interface frame 604A. Such a customized shape surface on the eye region interface frame 604A can help ensure repeatable location of the eye region interface frame 604A from measurement-to-measurement, such as can occur over a short-term acute period of time or a much longer term chronic period of time.

The mid-frame 604B can include a connector frame that can slide vertically into corresponding receiving slots or tracks in the eye region interface frame 604A. The mid-frame 604B can include female indexing features corresponding to male indexing features on the eye region interface frame 604A, such as at equally-spaced or other fixed-position indexing stop/pause step locations along the receiving slots or tracks in the eye region interface frame 604A. Such fixed position indexing locations can help allow for image capture at such different stop/pause step locations, which, in turn, can help increase the total image-include angle of capture to up to 200 degree off-center from an a center axis extending outward coaxially from a pupil of the subject's eye 200.

The device interface frame 604C can include a indexing fundus camera movement stage 416, to which a fundus camera or other ophthalmoscope or other eye imaging device can be attached. The indexing fundus camera movement stage 416 can laterally slide horizontally with respect to the mid-frame 604B, such as along the plane P2 parallel to the coronal plane of the patient. The indexing fundus camera movement stage 416 can include fixed-position stop/pause step indexing locations along this horizontal direction of motion, such as can be equally-spaced with a defined pitch between such stop/pause steps. This allows sliding of the indexing fundus camera movement stage 416 horizontally in well-defined steps, such as for acquiring images at such equally-spaced or other well-defined locations. A position encoder can record the corresponding positions of the indexing fundus camera movement stage 416 at the various steps, so that such information can be stored in memory in correspondence with the image data from the images acquired at such indexed step locations. The indexing fundus camera movement stage 416 can include an imaging opening, through which camera still or video eye images can be acquired, and an interface slot into which a fundus camera or other ophthalmoscope or other image-acquisition optics (or adapter therefore) can be inserted and held in position upon the indexing fundus camera movement stage 416. The indexing fundus camera movement stage 416 can hold the fundus camera or other imaging device such that it slides with the indexing fundus camera movement stage 416 and moves while maintaining a perpendicular orientation with respect to the coronal plane of the patient and a parallel orientation with respect to the sagittal plane of the patient. As described here, a micromotor can be connected to the indexing fundus camera movement stage 416, such as to move the indexing fundus camera movement stage 416, including stopping or pausing at one or more or all of the indexing locations along the horizontal direction, and such position information can be captured, such as by a microcontroller controlling the indexing fundus camera movement stage 416 or a digital encoder, and stored together with the corresponding images at such locations.

FIG. 7A (stage left), FIG. 7B (stage middle), and FIG. 7C (stage right) illustrate an example of various positions of the indexing fundus camera movement stage 416 of the device interface frame 604C with respect to the mid-frame 604B and the eye region interface frame 604A of the fundus camera mount 306 assembly. A fundus camera or other imaging optics can be attached to the indexing fundus camera movement stage 416 such as for acquiring eye images through the opening shown in the indexing fundus camera movement stage 416 at these or others of the various positions along the horizontal direction in which the indexing fundus camera movement stage 416 moves under control of a micromotor or otherwise, such as explained herein. Such motion of the indexing fundus camera movement stage 416 allows for a panoramic view, such as can be stitched together from individual images at various indexing positions of the indexing fundus camera movement stage 416.

Figures 8A, 8B:
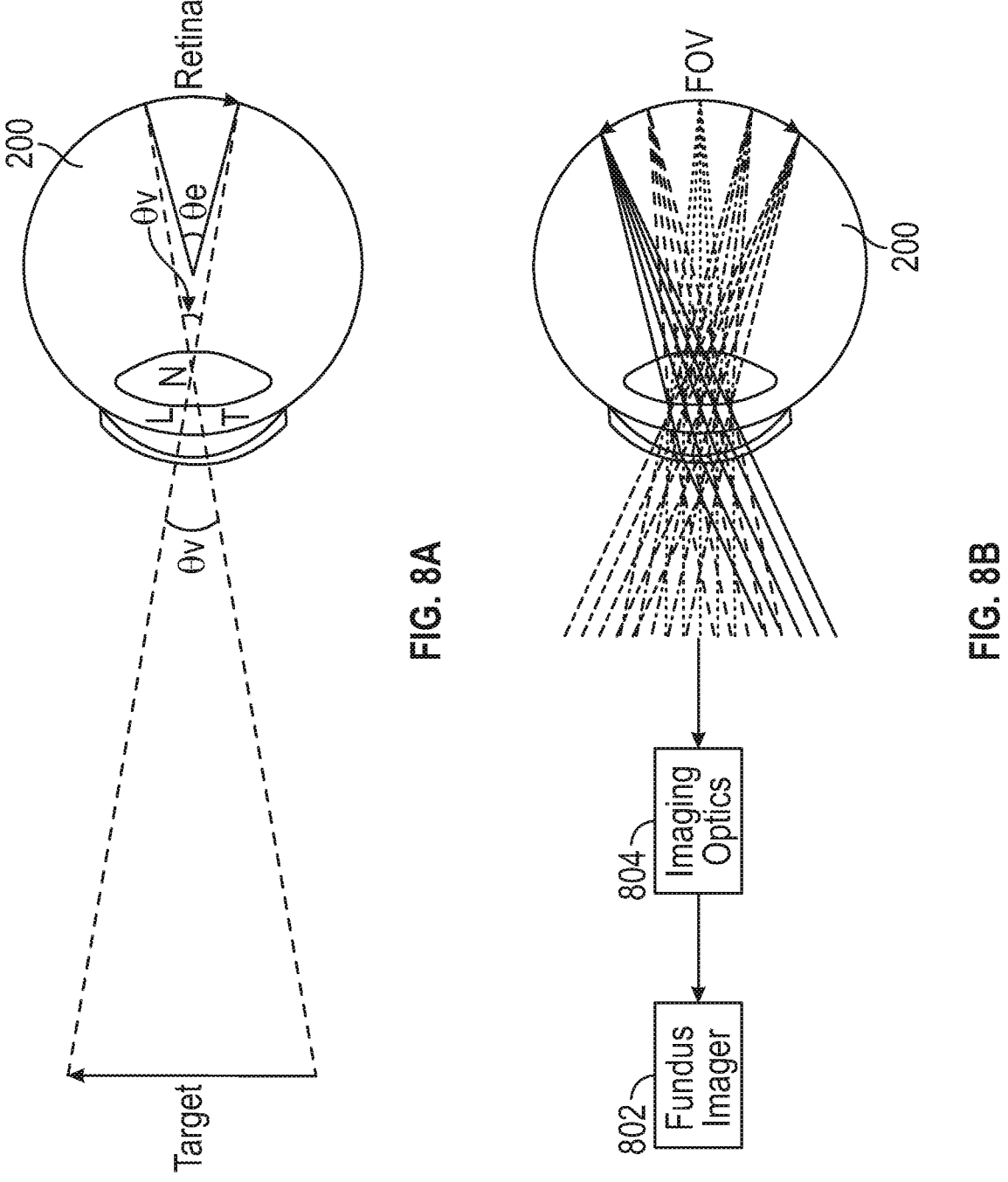
FIG. 8A shows a visual field of view of an eye (viewed from the top, looking in an inferior direction and in a transverse plane).
FIG. 8B shows a corresponding similar view of the eye, showing various imaging angles obtainable by translating the indexing fundus camera movement stage.

FIG. 8A shows a visual field of view of an eye 200 (viewed from the top, looking in an inferior direction and in a transverse plane). FIG. 8B shows a corresponding similar view of the eye 200, showing various imaging angles obtainable by translating the indexing fundus camera movement stage 416 in the horizontal direction parallel to the coronal plane, as described above. A fundus camera or other fundus imager 802 and any accompanying imaging optics 804 can be mounted upon the indexing fundus camera movement stage 416 for acquiring such images through the hold in the indexing fundus camera movement stage 416, as explained above.

Figure 9:
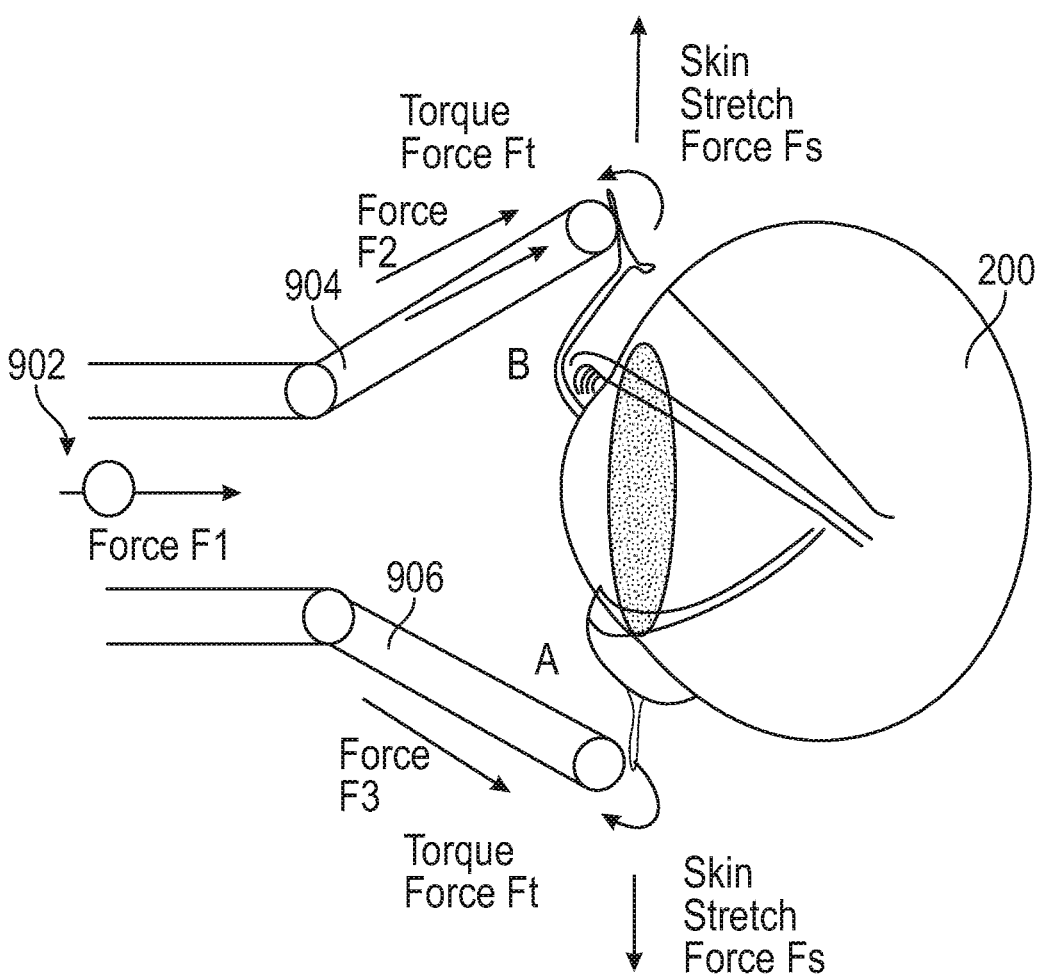
FIG. 9 shows an example of an eyelid or skin stretching mechanism.

FIG. 9 shows an example of an eyelid or skin stretching mechanism 902 or spreader, such as which can optionally be pivotably or otherwise attached to the patient-facing conformal eye region interface frame 604A for helping to engage and open or hold-open an upper eyelid, a lower eyelid, or both of a patient eye 200, such as during eye image acquisition. The eyelid or skin stretching mechanism 902 can include shaped elastomeric finger tabs, such as an upper eyelid finger tab 904 and a lower eyelid finger tab 906, each of which can protrude from the conformal patient-facing conformal eye region interface frame 604A toward their respective eyelid, such as to help displace the corresponding eyelid open during image acquisition.

When the conformal patient-facing conformal eye region interface frame 604A is pressed against the bony region around the patient eye 200, a force F1 is applied in a direction toward the patient eye 200. The upper eyelid finger tab 904 transmits a force component F2 of the force F1 in an appropriate direction such as to displace, open, or hold-open the upper eyelid of the patient eye 200, such as with a skin stretch force component Fs in the coronal plane in a superior direction away from the patient eye 200. The lower eyelid finger tab 906 transmits a force component F3 of the force F1 in an appropriate direction such as to displace, open, or hold-open the lower eyelid of the patient eye 200, such as with a skin stretch force component Fs in an inferior direction in the coronal plane away from the patient eye 200. The applied force F1 can be well-defined, for example, it can be measured by a force or pressure sensor that can be included in the eye region interface frame 604A or even embedded into one or both of the upper eyelid finger tab 904 or the lower eyelid finger tab 906. When the appropriate pressure has been applied, a confirmation signal can be delivered to the patient or other user or to controller circuitry controlling application of the applied force F1. For example, a user confirmation signal to the patient can include one or more of an audible signal, a visual signal, or a haptic signal.

The normal force F1 translated into the angular component F2 multiplied by the applied angle plus the adhesion force between the elastomer of the upper eyelid finger tab 904 or the lower eyelid finger tab 906 and the skin, which can be configured such as to exceed the force Fs needed to stretch the skin. The elastomer durometer and surface of the upper eyelid finger tab 904 or the lower eyelid finger tab 906 determines the adhesion force of the elastomer to the skin about the patient eye 200. The skin interface surface of the upper eyelid finger tab 904 or the lower eyelid finger tab 906 can be specified such as to create a degree of adhesion, such as can include but is not limited to physical or gecko adhesion. A relationship between the forces can be represented by:

$$Fs < F1 \cdot \cos\theta + F \text{ adhesion(skin to elastomer)} \qquad (1)$$

$$Fs < F1 \cdot \sin\theta + F \text{ adhesion(skin to elastomer)} \qquad (2)$$

The upper eyelid finger tab 904 and the lower eyelid finger tab 906 can be configured and operated such that the adhesion force far exceeds the applied force F1 and the skin stretch force Fs.

Figures 10A, 10B:
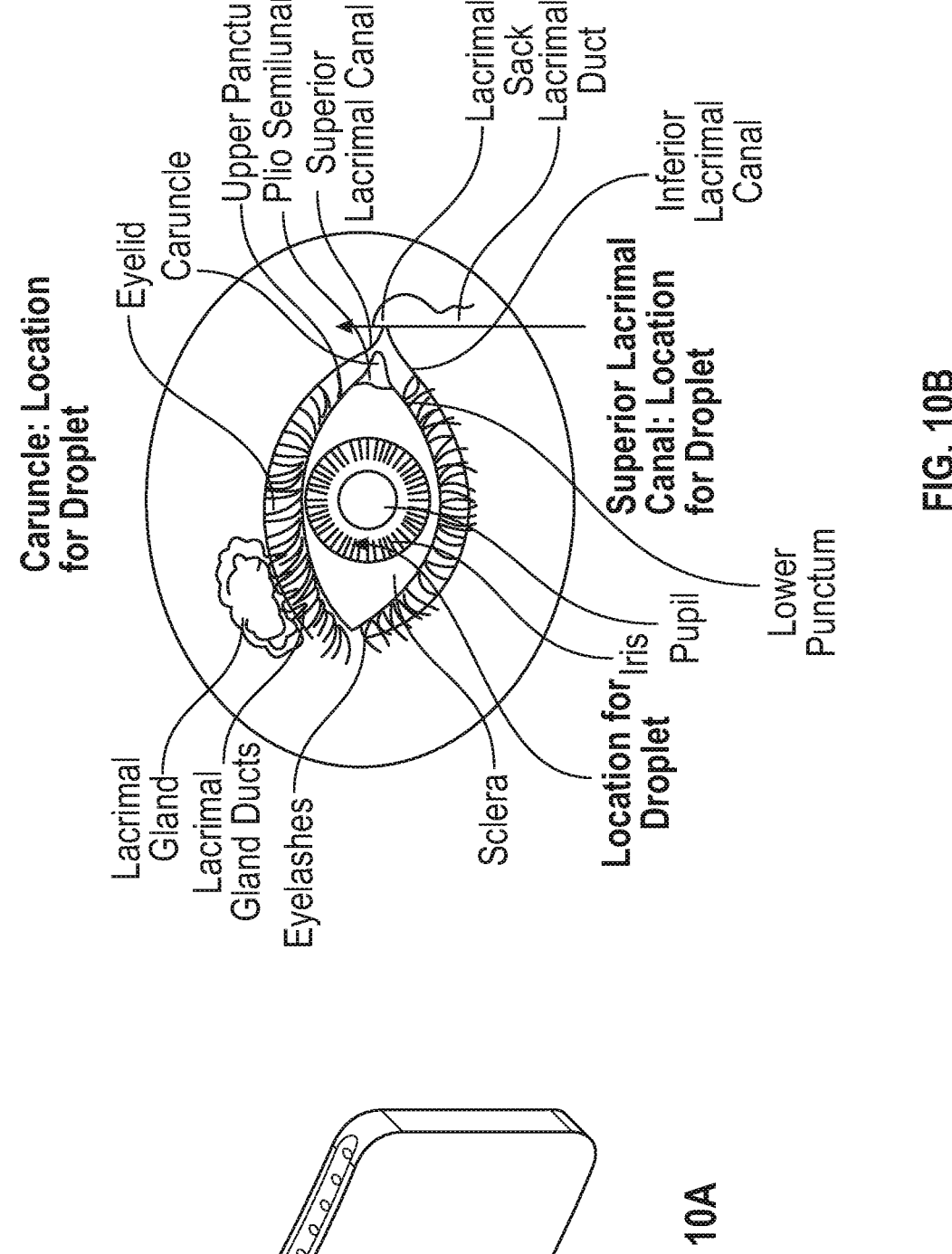
FIG. 10A shows an example of a perspective view of an liquid or mist dispensing adapter.
FIG. 10B shows a view looking toward the eye with some potential locations for dispensing a liquid or mist toward.

FIG. 10A shows an example of a perspective view of an liquid or mist dispensing adapter 1002 for dispensing fluid into or toward the eye 200, such as can optionally be included on the conformal patient-facing eye region interface frame 604A or as part of the eyelid or skin stretching mechanism 902 or elsewhere in proximity to the eye 200. FIG. 10B shows a view looking toward the eye 200 with some potential locations for dispensing a liquid or mist toward, such as toward the cornea, toward the caruncle, or toward the superior lacrimal canal of the eye 200.

The adapter 1002 can include or be connected to a dropper or mister or gas dispenser 1004. The dispenser 1004 can be configured with a nozzle, such as to permit medicated or unmedicated liquid eye drops or a mist into the eye 200, or to dispense air or gas toward the eye 200, such as to optionally dry the eye 200 or to use the puff of air or gas to perform a tonometry pressure measurement of the eye 200 such as to measure intraocular pressure of the eye 200 or to measure one or more mechanical properties of the eye 200. The horizontal sliding provided by the indexing fundus camera movement stage 416 or the vertical sliding of the mid-frame 604B with respect to the eye region interface frame 604A can permit movement of dispenser 1004 with respect to the eye 200 such as to allow positioning for dropping or misting toward the eye 200, which can be carried out with the eyelids open or with the eyelids closed, as desired. For example, the eye drops can be directed toward or into the caruncle location of the eye 200 with the eyelids closed. Upon opening the eye 200 after the drop has been dispensed in the caruncle cavity the dispensed liquid can flow into the eye 200. This makes it easy to put medication or other drops into the eyes of patients who are not able to easily self-administer such eye drops. The adapter 1002 and the dispenser 1004 also permit dispensing drops or mist toward or into a center of the eye, such as for those patients who are comfortable with keeping the eyelids open during such dispensing. The eyelid or skin stretching mechanism 902 can also be helpful in keeping the eyelids open for dispensing liquids, gas, mist, or puffs toward or into the eye 200.

In FIGS. 5A-5B, the internal liner 307 or the outer shell 305 of the helmet 300 can include or be coupled to one or more sensors 500, such as pressure or force sensors, a gyroscope, an accelerometer, or the like. For example, a 3-axis combined gyroscope/accelerometer can be included in the helmet 300 or the fundus camera mount 306, or both. An example of such a combined gyroscope accelerometer integrated circuit (IC) device can include MPU-6050 (available from Maxim Integrated Circuits/Analog Devices, Inc.). The accelerometer and gyroscope individually bring strong advantages to the present system; however, both have areas of data uncertainty. With both such sensors collecting data on the same object movement phenomena, the data from the accelerometer and gyroscope can be merged, qualified, or otherwise fused using an appropriate sensor fusion approach.

Sensor fusion techniques can be used to combine sensing data from disparate sources and generate information that has less uncertainty and, therefore, more accuracy. In the case of gyroscopes and accelerometers, each of these devices can serve to offset the other's noise and drift errors, such as to help provide more complete and accurate movement tracking, which, in turn, can permit more accurate image acquisition, image-processing, image-analysis, and diagnosis. For example, the data respectively output by the accelerometer(s) and the gyroscope(s) can be combined using a Kalman filter or other complementary filter, such as can be included in the controller circuitry 508 or in other signal-processing circuitry communicatively coupled thereto. The Kalman filter is a powerful tool that allows combining information in the presence of uncertainty. In a dynamic system, a Kalman filter can be helpful as conditions change.

When combining the 3D accelerometer and 3D gyroscope data, it is helpful to have both sensors located in the same device. An illustrative example of such a combined device is the LSM6DS3HTR 3D accelerometer and 3D gyroscope from STMicroelectronics, which can allow, among other things, pedometer, motion tracking, gesture detection, tilt detection, and other functionality. The LSM6DS3HTR can be configured to provide a dynamic user selectable full-scale acceleration range of ±2/±4/±8/±16 g, and an angular rate range of ±125/±245/±500/±1000/±2000 dps. When combining a 3D accelerometer and a 3D gyroscope, the complementary (or Kalman) filter can be configured to initially use data from the gyroscope for precision, because the gyroscope is not as vulnerable to external forces. On a longer-term basis, the accelerometer data can be useful because the accelerometer data does not drift in the same manner and extent as data from a gyroscope.

In an illustrative example, the complementary (or Kalman filter can be represented as:

$$angle=0.98\times(angle+gyrData\times dt)+0.2\times(accData) \qquad (3)$$

to determine an angle of a position from gyroscope data (gyrData), accelerometer data (accData), and time interval (dt). These values can be integrated over time, such as by the controller circuitry 508. In an example, the controller circuitry 508 can be battery-powered and can include an STM32 microcontroller from STMicroelectronics, such as to process data from the sensors 500, such as which can include a pressure or force sensor carried by one or more of the nested frames 604, a gyroscope or accelerometer, or for controlling or receiving data from a micromotor, such as for positioning the indexing fundus camera movement stage 416. Based on information received from the sensors 500, the controller circuitry 508 can determine or confirm whether the various componentry of the helmet 300 system, including the fundus camera, is properly positioned to be ready for image acquisition. The controller circuitry 508 can issue a visual or audible or other positioning confirmation alert to the patient or other user to inform the user that the various componentry of the helmet 300 system is properly positioned and ready for image acquisition. The controller circuitry 508 can include a Bluetooth or other communication interface. This can permit the controller circuitry 508 to be communicatively coupled to a local Bluetooth-enabled user-interface device, which, in turn, can be communicatively coupled via a mobile telephony or other communication network to a cloud-based server, such as for data storage or processing.

FIG. 11 is a flow chart illustrating generally an example of a process 1100 of forming the conformal components used in the helmet 300 system. For this process 1100, an elastomeric frame with embedded transponders can be provided to the patient or a technician assisting the patient for whom the helmet 300 system is being provided. At 1102, an elastic wearable headliner can be placed, with transponders with its centroids forming triangular shell elements, on the surface of head hemisphere of the target patient. Additionally or alternatively, at 1104, an eyepatch with transponders with its centroids forming triangular shell elements can be placed upon the target patient. In either case, the transponders" antennas are able to connect with a scanning device such as a smart phone or an other device with a camera and scanning capability. At 1106, the target patient can be scanned using the scanning device that connects with the transponders, such as to locate and create a 3D virtual map of one or more positions on the head of the target patient. The shell elements formed by the transponders can then create a surface on the 3D virtual map that can be converted to a solid surface via software and imported into any Computer Assisted Design (CAD) software. At 1108, the 3D virtual map surface created by the scan can be exported to a CAD software package to incorporate the surface into the design. At 1110, the design can be exported to a 3D printer or a machining or molding apparatus. At 1112, the 3D printing or molding can be used to manufacture the customized part, in which the scanned surface can be incorporated into the internal liner 307 of the helmet 300 or the conformal eye region interface frame 604A customized to seat against the bony features about the eye 200, either of which can be 3D-printed or molded, such as to include the embedded sensors 500 such as described herein. At 1114, minor adjustments or calibration can be made such as to finalize the best custom fit for the particular target patient.

FIG. 12 is a flow chart illustrating generally an example of a process 1200 for eye image capture. At 1202, the helmet 300 can be placed upon the head of the patient, and positioned or re-positioned until an audible alarm generated by the controller circuitry 508 is heard, indicating proper placement and positioning of the helmet 300 on the head of the patient. At 1204, the first arm member 402 can be lowered from the first pivot point 404 and the second arm member 408 and the second pivot point 406 can be adjusted to place the fundus camera mount 306 against the bony structure around the eye 200, with proper positioning being indicated by the controller circuitry 508 generating an audible or visual alert signal to indicate proper placement and positioning. At 1206, a fundus camera or other image capture device can be placed on the indexing fundus camera movement stage 416. At 1208, the user can push against the fundus camera or other image capture device slightly, until the controller circuitry 508 issues a final audible alarm indicating proper positioning of all sensors and other componentry of the helmet 300 system. Then, auto-focusing can begin, such as for beginning to take still or video eye images of the eye 200 under the control of the controller circuitry 508. At 1210, the controller circuitry 508 can control sliding horizontal movement of the indexing fundus camera movement stage 416 to move incrementally between the indexed positions. At each indexed position, an eye image can be captured. This can be repeated, until the entire eye angle is covered. At 1212, the eye images captured at the various indexed positions can be stitched together in software, such as to create a panoramic view that covers the full eye angle, such as can capture all of the vasculature within the eye 200. At 1214, the captured images are automatically reviewed by controller circuitry 508 and, if of sufficient image quality, are approved and uploaded to a local user interface device, which, in turn, can upload the images to a remote server.

Figure 13:
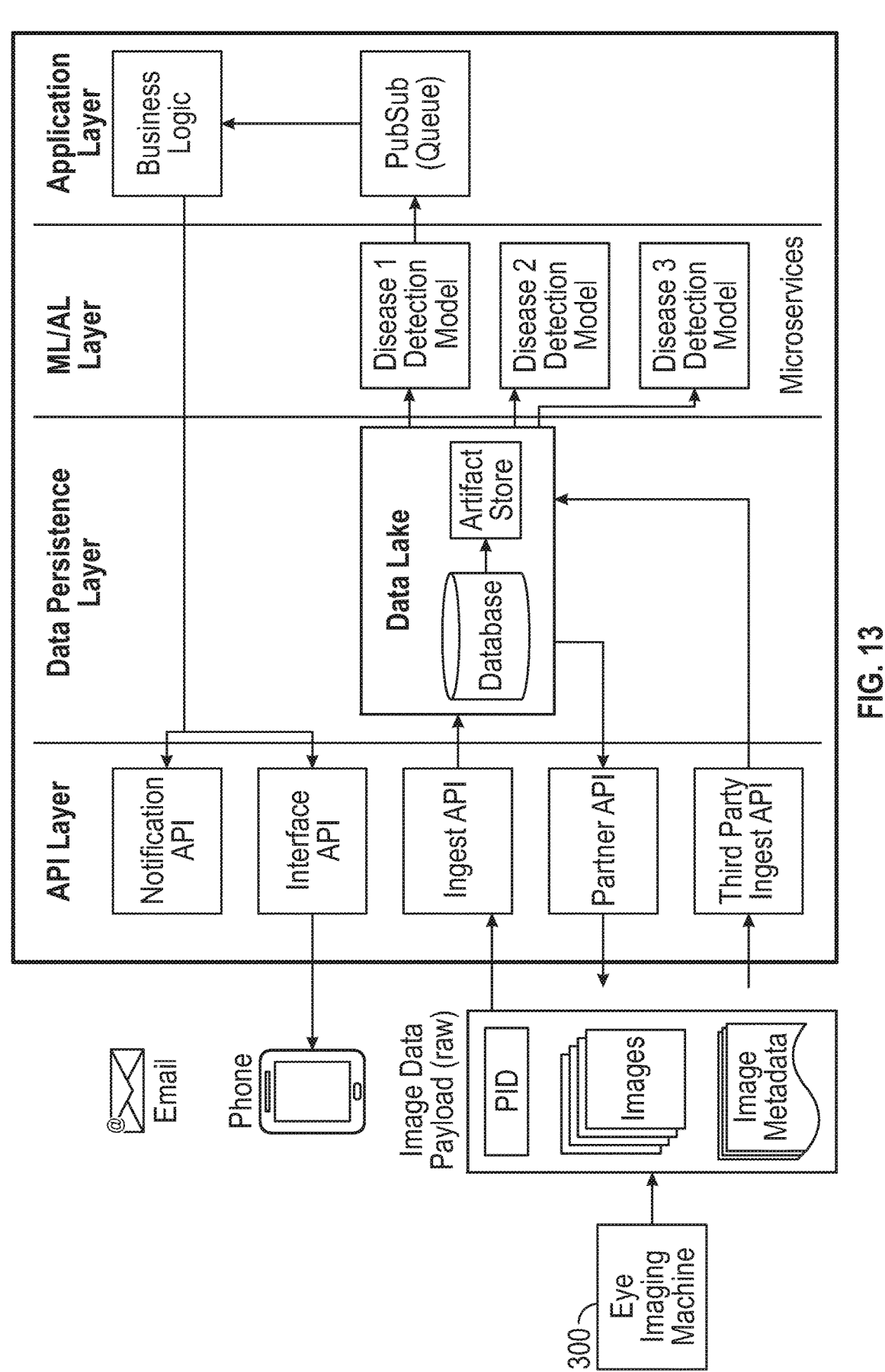
FIG. 13 is a block diagram illustrating an example of the helmet system for eye image capture, together with other portions of the system for image-processing, image-analysis, and diagnosing or monitoring a disease or physiological condition.

FIG. 13 is a block diagram illustrating an example of the helmet 300 system for eye image capture, together with other portions of the system 1300 for image-processing, image-analysis, and detecting or classifying or diagnosing or assessing monitoring a disease or physiological condition, such as can include one or more of: one of diabetes, diabetic retinopathy, high blood pressure, stroke, glaucoma, sickle cell disease, thyroid disorder, cancer, arthritis, multiple sclerosis, high cholesterol, brain tumor, cognitive impairment, Alzheimer's disease, or concussion.

In FIG. 13, the system 1300 can include the helmet 300 and the other portions of the system described above. The raw image data generated can be first analyzed by a local embedded processor included in the system and also additionally or further submitted to a local or remote server, such as for further processing, storage, or both. A local or remote storage unit can store the raw data and the image metadata. An application programming interface (API) layer can provide an interface to import the metadata into a data lake. The API can also allow for third-party data to be exported or imported into the data lake, such as for further processing. The post-processed metadata can be provided to a machine learning layer such as for processing and inference generation. The inferences can be communicated through the application layer and then to the API layer, such as to provide notification to the subject or a caregiver about the inference. The inference can be validated by either the system supplier-approved panel or the subject's healthcare provider. Further tests can optionally be conducted to reach or further support a diagnosis. The data can be tagged on to the inference, which, in turn, can be used to help improve the ML model. This data can be made available for the subject to use as the subject deems appropriate, including providing to the subject the potential for monetization of the data. A supplier can employ the system and can act as a distributor of the data through its secure data and contract management software platform. The continuous collection of data and the machine learning algorithm and model can be combined to create or support a health management system for any individual that can aid in early detection of various diseases, such as can help allow expanding the overall reach of health care at a low cost.

Figure 14:
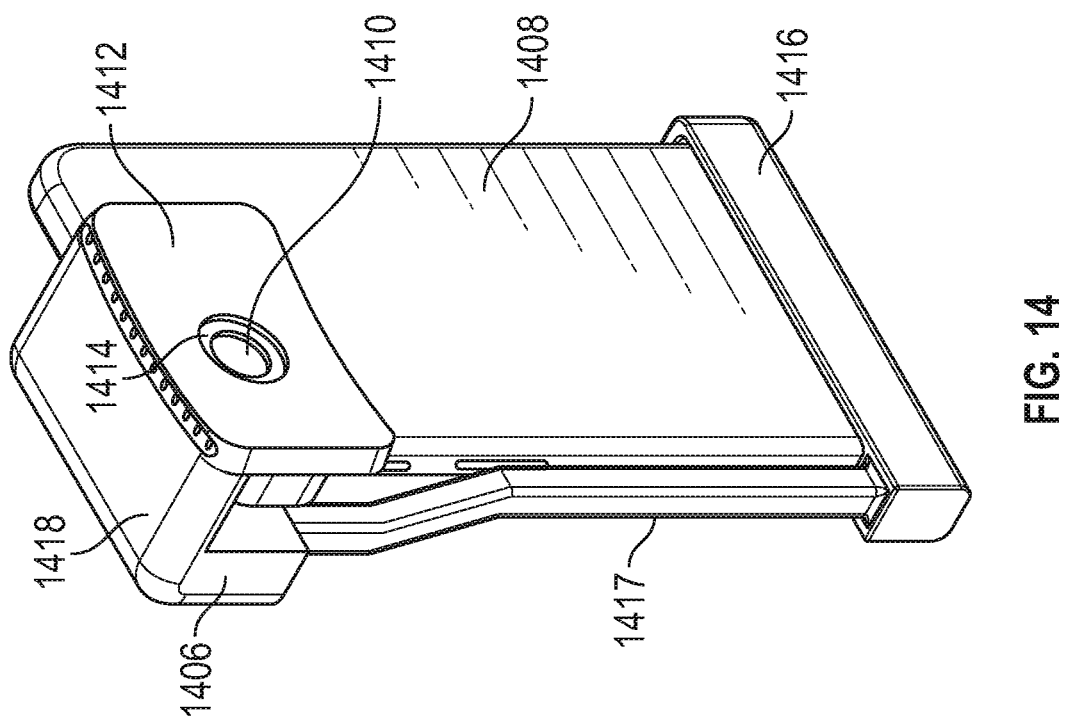
FIG. 14 shows an example of an eye imager mount for a mobile phone such that a camera of the mobile phone can be used as a fundus camera for eye imaging.

FIG. 14 shows an example of an eye imager mount 1406, which can be used as the fundus camera mount 306, such as described herein. The eye imager mount 1406 can optionally be sized, shaped, and otherwise configured to provide a mobile phone holder or receptacle to hold and carry a mobile phone 1408. In this way, a camera lens 1410 of the mobile phone 1408 can be pointed toward the patient eye and used as the fundus camera or other eye imaging device. The eye imager mount 1406 can include a patient-specific or other conformal camera guide fixture or brace 1412. The brace 1412 can be conformally or otherwise shaped to fit securely against a patient's eye socket in a repeatably reliably positionable manner. The brace 1412 can include a camera lens opening 1414 that aligns with a camera lens 1410 of the mobile phone 1408, such as to allow the camera of the mobile phone 1408 unobstructed access through the camera lens opening 1414 to acquire still or moving images of a retina or other interior region of a patient's eye, as described herein.

Figure 15:
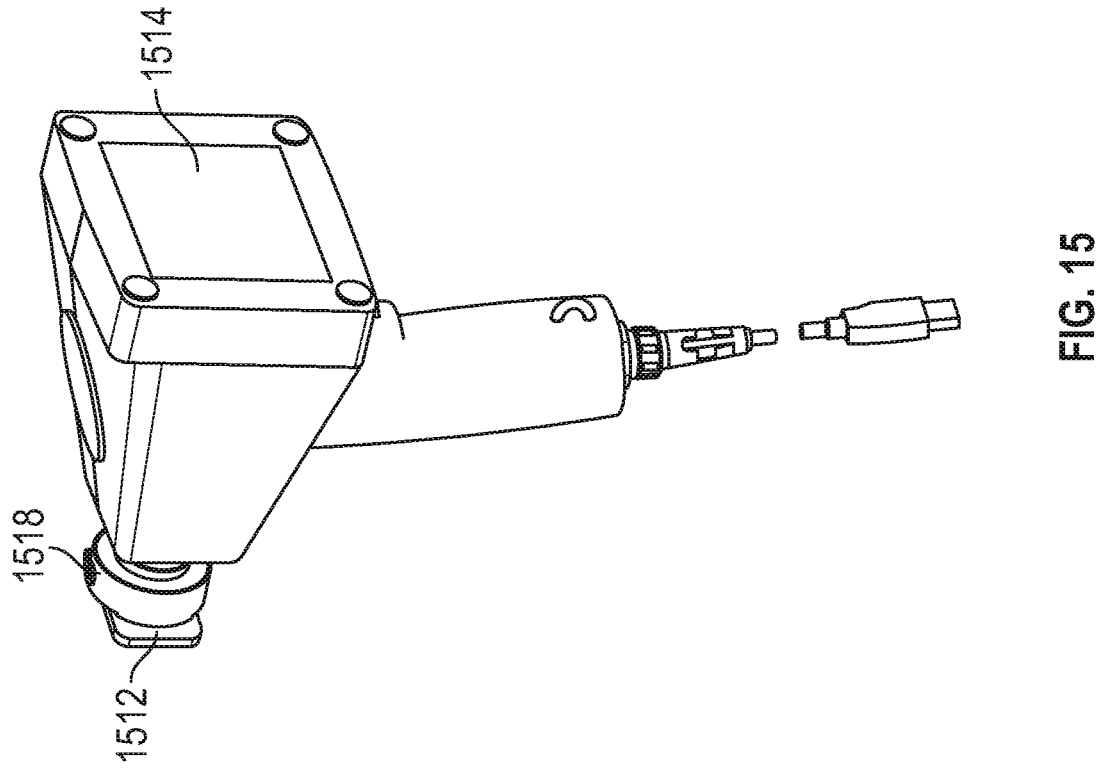
FIG. 15 shows an example of a brace that can be coupled to a hand-held fundus camera or other eye imager, such as via a ball-joint.

The brace 1412 can be adjustably coupled to other portions of the eye imager mount 1406, such as by a ball-joint. This can allow additional ability to move the mobile phone 1408 and its camera to allow the mobile phone camera to point toward different regions within the interior region of the patient's eye, if desired. The aspect of coupling a custom-fitted or other brace 1412 to an eye imager such as a camera via a ball-joint or other adjustable joint can also be applied in the context of other handheld fundus camera or other handheld eye imager devices, such as shown in FIG. 15. The example of FIG. 15 shows a brace 1512 coupled to a handheld fundus camera 1514, such as via a ball-joint 1518.

In FIG. 14, the eye imager mount 1406 can include a mobile phone carrier portion that can include a bottom support bracket 1416 to carry the mobile phone 1408. The bottom support bracket 1416 can be coupled to and spaced apart from a top support bracket 1418 by a frame 1417 that can be coupled to the brace 1412. The eye imager mount

1406 can be coupled to a helmet 300 via an articulating arm, such as described herein. Alternatively, if desired, the eye imager mount 1406 and the mobile phone 1408 can be used as a standalone handheld device for performing eye imaging, such as shown in FIG. 14, without requiring attachment to a helmet 300 via an articulating arm.

Figure 16:
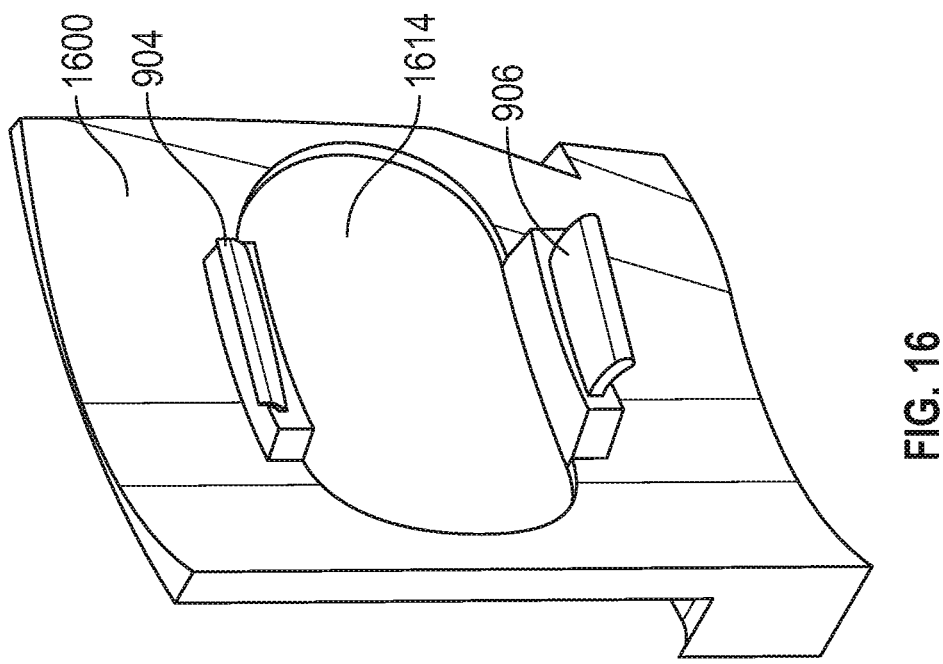
FIG. 16 shows an example of an eyepiece.

FIG. 16 shows an example of an eyepiece 1600, such as which can be used as the brace 1412. For example, the eyepiece 1600 can be used as or with the fundus camera (or other eye imager) mount 306 or the brace 1412 described herein. Also, the eyepiece 1600 can include one or more eyelid retractors, such as described above with respect to the eyelid or skin stretching mechanism 902 of FIG. 9. As described above, the eyelid or skin stretching mechanism 902 can include shaped elastomeric finger tabs, such as an upper eyelid finger tab 904 and a lower eyelid finger tab 906, each of which can protrude from the conformal patient-facing conformal eye region interface frame toward their respective eyelid, such as to help displace the corresponding eyelid open during image acquisition. In the example of FIG. 16, the upper eyelid finger tab 904 and the lower eyelid finger tab 906 are shown as at least having at least a portion that is elastomeric or otherwise flexible to appropriately engage with a desired eyelid or other skin region to be retracted out of the way for capturing unobstructed images of the eye through the camera lens opening 1614. The elastomeric or other flexible upper eyelid finger tab 904 can include an upward angle or curl in the projecting upper eyelid finger tab 904 to orient the tab to push the upper eyelid in an upward direction. The elastomeric or other flexible lower eyelid finger tab 906 can include a downward angle or curl in the projecting lower eyelid finger tab 906 to orient the tab to push the lower eyelid in an downward direction. The upper eyelid finger tab 904 and the lower eyelid finger tab 906 can be customized in size or shape, such as to better fit a particular eye of a particular patient.

Figure 17:
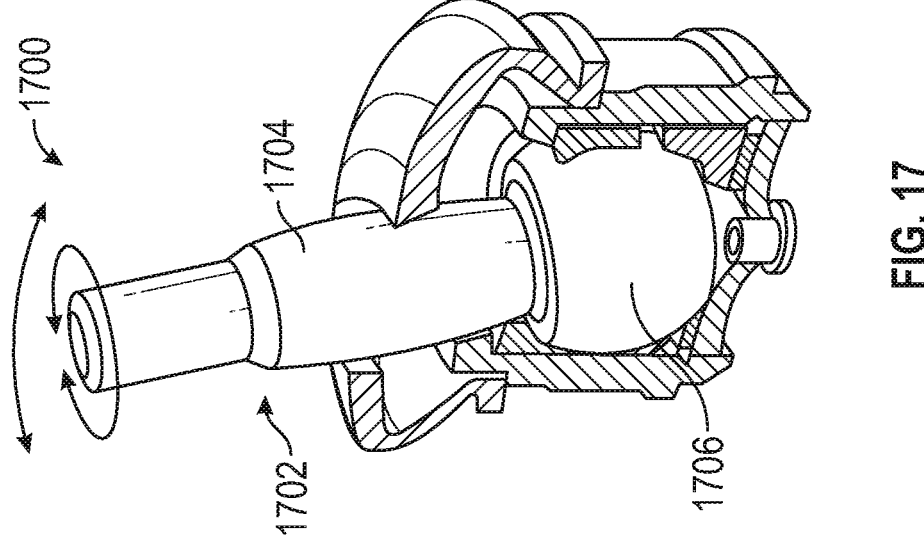
FIG. 17 shows an example of an eye imager device that can include an ultrasound imaging device.

FIG. 17 shows an example of an eye imager device 1700 that can include an ultrasound imaging device that can be used in addition to, or as an alternative to, a fundus camera, mobile phone, or the like such as described herein. Thus, the eye imaging performable by the present system, such as can include the helmet 300 and other components, can include not only two-dimensional (2D) still or moving photographic or video images, but can also include three-dimensional (3D) imaging from an appropriate imaging modality, such as ultrasound imaging, optoacoustic imaging, optical coherence tomography (OCT) with enhanced-depth imaging (EDI), or another 3D imaging modality. The eye imaging performable by the present system can additionally or alternatively include spectroscopic analysis or other analytic capability, if desired, such as for analyzing fundus autofluorescence (FAF), visual field testing, fluorescein angiography (FA), or indocyanine green angiography (ICGA).

For example, ultrasound retinal imaging can help provide morphological information of the optic nerve and other features in the eye in three dimensions (3D), such as without requiring dilation of the eye. Ultrasound or other 3D imaging modalities can help when diagnosing and managing posterior segment pathology, and can be useful alone or together with neuroimaging or tests of visual function. Some conditions, such as age-related macular degeneration (AMD) and diabetic retinopathy (DR), may have one or more unique aspects that manifest in 3D diagnostic imaging that otherwise may not be observable clinically by eye imaging only. Additionally, more complicated pathologies may otherwise involve a battery of tests to eliminate differentials and arrive at the correct diagnosis.

In FIG. 17, the ultrasound eye imaging can help provide the ability to capture clear images, including for the anterior segment of the eye, including images of structures concealed by the iris or corneal opacities, as well as posterior portions of the retina, even when optical clarity is compromised. Such ultrasound based retinal imaging can be used to identify a number of diagnostic indications.

For example, ocular ultrasound may be useful for, among other things:

calculating the power of an intraocular lens;

evaluating the posterior segment in cases with media haze;

evaluating the cornea, such as for corneal scar, hazy cornea, corneal edema, or another condition of the cornea;

evaluating the anterior chamber of the eye, such as for hyphema (accumulation of red blood cells) or for inflammation of the anterior segment;

evaluating a cataract, such as a dense cataract;

evaluating the pupillary membrane or posterior synechia;

observing retrolental membrane or posterior capsular opacity;

evaluating vitreous hemorrhage or severe vitreous membranes or exudates;

characterizing the nature of an ocular mass or optic disc lesion;

differentiating retinal detachment (RD) of rhegmatogenous etiology from an exudative retinal detachment, or to differentiate RD from retinoschisis;

detecting or localizing intraocular foreign bodies;

evaluating orbital lesions; and evaluating the retina, choroid, or sclera in various conditions such as which may include one or more inflammatory diseases.

The ocular ultrasound imaging can include one or both of Amplitude (A) scan ultrasound or Brightness (B) scan ultrasound. A-scan ultrasound shows the amplitude of the ultrasound echoes as the vertical height from a baseline to represent the strength of the echoes. The horizontal distance between two echoes can be used to measure the distance between two structures, such as in a measurement of ocular axial length using an A-scan ultrasound probe during ocular biometry before cataract surgery. B-scan ultrasound can provide a 2D display showing the size and echotexture of a lesion. Because ultrasound waves have a difficult time traveling through air, ultrasound gel can be used to reduce the air between patient and the ultrasound transducer. This can help to reduce acoustic impedance and reflection to allow for a clear ultrasound image to be produced.

Ultrasound scanning can be particularly useful when a patient has a condition that prevents examination of the internal structures of the eye. Examples may include patients with opaque corneas, dense cataracts, or vitreous hemorrhages that may obscure a visual view of the posterior segment using slit-lamp examination or biomicroscopy. In these cases, B-scan ultrasonography can be used. B-scan ultrasound is capable of providing valuable information about the lens, vitreous, retina, choroid, sclera, and orbit. B-scan ultrasonography is a painless, noninvasive method that can be performed easily in the clinic, or at a hospital bedside. It can be done safely on adults and children. It can also be a powerful diagnostic tool even when pathology is clinically invisible using optical-based visualization techniques. In the present context, the helmet 300 and associated articulating eye imager fixture and componentry can be adapted and used for ultrasound retinal imaging, such as with an eyepiece attachment that is specific to an ultrasound scanning probe.

In FIG. 17, a commercially available B-scan ultrasound probe (e.g., from DGH Technology, https://dghtechnology-.com/products/scanmate-b/) can be attached to an appropriately adapted eyepiece, stage, or brace, such as which can optionally be articulatably coupled to the helmet 300. This can enable adding 3D characterization of the posterior of the eye or retina, such as for assessing optic nerve stress over time as well as myopia. Such ultrasound capability can complement or enhance the diagnostic characterization of the eye, such as compared to solely using 2D imaging from a visual or camera inspection of the eye through the pupil. The dispenser 1004 shown and described above with respect to FIG. 10A can be used to dispense an impedance-matching gel between the ultrasound probe and the eye so that the ultrasound energy from the probe more easily couples into the structure of the eye for performing the ultrasound imaging. Additionally or alternatively, an ultrasound gel-pack can be provided and positioned between the ultrasound probe and the eye, such to provide an impedance-matching gel in the gel-pack for acoustic impedance matching and improved ultrasonic imaging.

The eyepiece, stage, or brace can include appropriate coupling features to attach the ultrasound probe to the eyepiece, stage or brace. In FIG. 17, the eye imager device 1700 can include an ultrasound probe 1702, such as which can include a handle 1704. The ultrasound transducer can be carried within the handle 1704 or housed within a ball joint 1706 coupling the handle 1704 to the eyepiece, stage, or brace. This can permit the ultrasound transducer to be "pointed" in a desired direction, such as by orienting, rotating, or otherwise manipulating the handle 1704, such as manually by an end-user, or by a robotic device that can include a micromotor and actuator to orient the handle 1704 with respect to the ball joint 1706. The componentry shown in FIG. 17 can be attached to the eyepiece, stage or brace, which, in turn, can be articulatably attached to the helmet 300, such as described herein. In this way, the positioning componentry described herein can be used to consistently locate a chosen eye imager device 1700 with respect to the patient eye.

Figure 18:
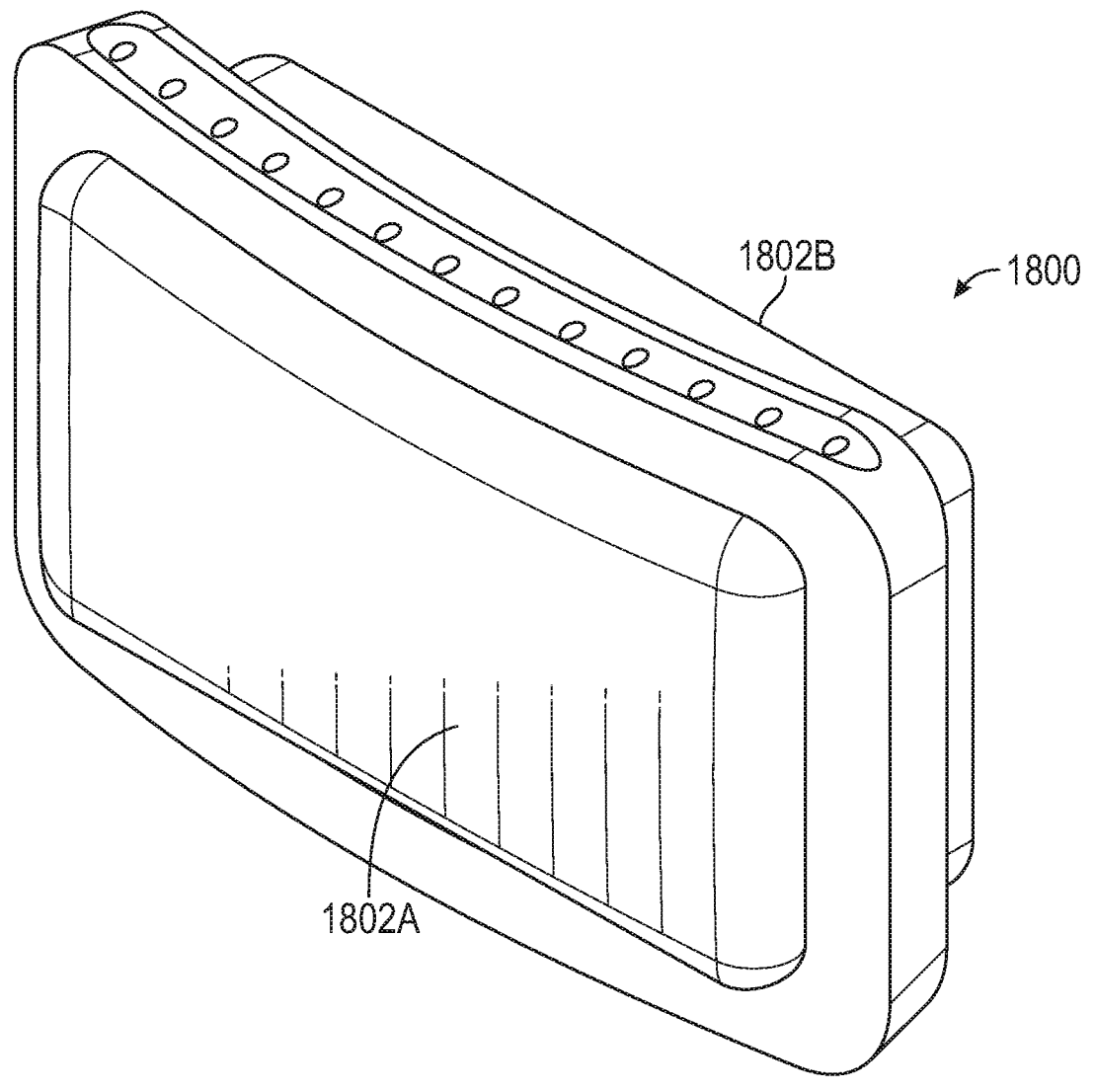
FIG. 18 shows an example of an ultrasound gel-carrying cartridge, such as which can be slid or snapped into or otherwise attached to the eyepiece, stage, or brace that, in turn, can be articulatably attached to the helmet.

FIG. 18 shows an example of an ultrasound gel-carrying cartridge 1800 (also referred to as a gel pack), such as which can be slid or snapped into or otherwise attached to the eyepiece, stage, or brace that, in turn, can be articulatably attached to the helmet 300, such as described herein. The ultrasound gel carrying cartridge 1800 can be located between the eyepiece, stage, or brace, and the patient eye. The ultrasound imaging probe 1702 can be located against the cartridge 1800, such as on a side of the cartridge 1800 facing away from the patient's eye. The cartridge 1800 can include soft conformable membrane features 1802A-B on each side—that is, a first conformable membrane 1802A on the side facing the patient's eye, and a second conformable membrane 1802B on the side facing the ultrasound imaging probe. For example, the membrane 1802A-B can include a soft olefinic membrane or a biodegradable thermoplastic monomer membrane such as a polylactic acid (PLA) and or a combination of such materials. The cartridge 1800 can displace air between the ultrasound imaging probe 1702 and the patient's eye, such as to help permit good acoustic impedance matching between the ultrasound imaging probe 1702 and the patient's eye.

The gel extrusion from either side (or both sides) can help provide continuity between the probe surface and the measurement surface. The gel can be provided or modified to help reduce, minimize, or eliminate distortion. The gel extrusion on either surface can occur by applying force or pressure from the ultrasound measurement probe. The gel cap membrane can also help prevent accidental eye damage due to unintended pressure applied onto or into the eye. The eyepiece, stage, or brace, can include interchangeable kit components, e.g., adapted for ultrasound imaging, adapted for camera imaging, or otherwise. In this way, the helmet fixture assembly and kit components described herein can provide an imaging modality agnostic image capture system.

Figure 19:
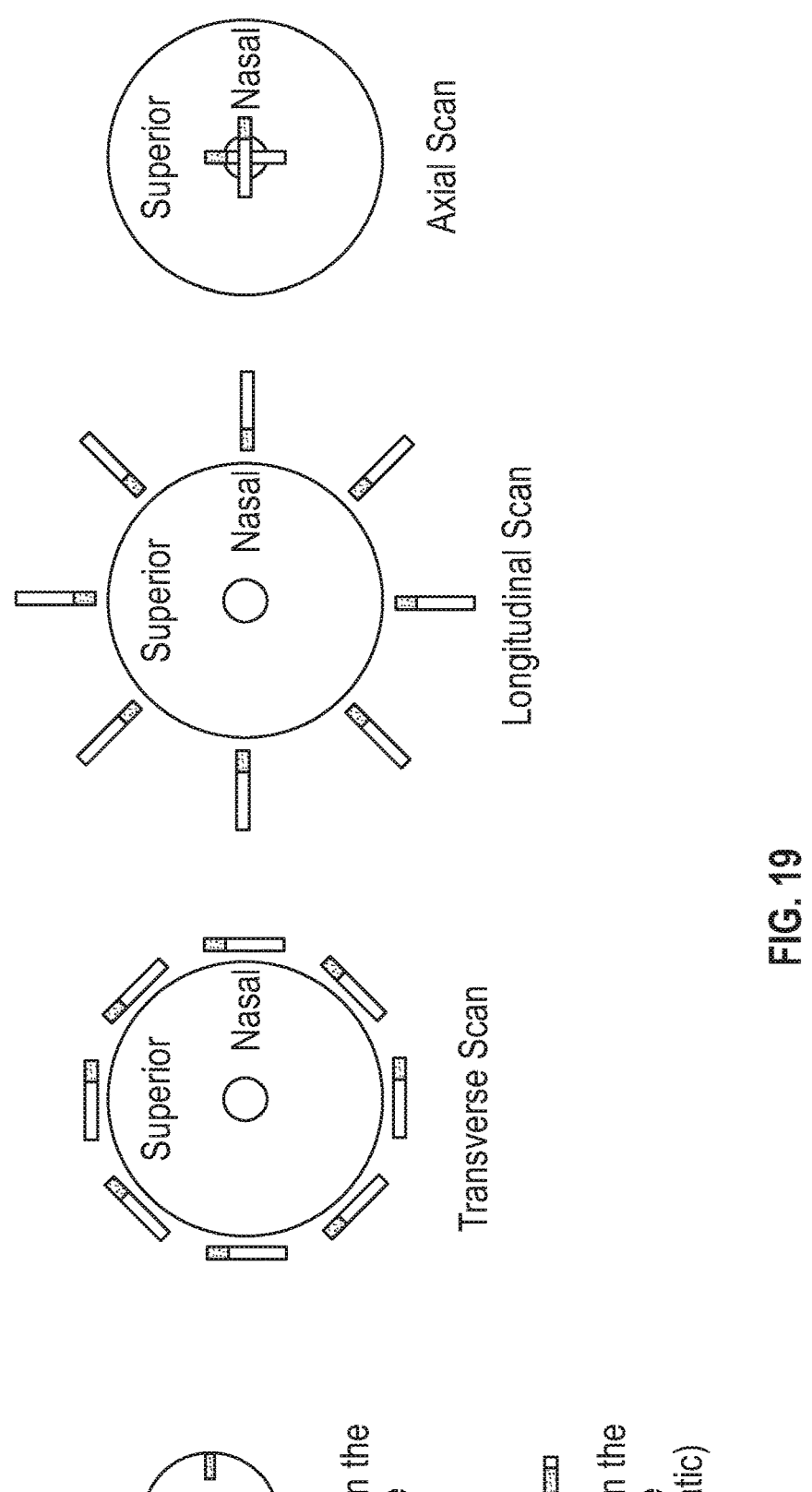
FIG. 19 illustrates three different orientations in which the B-scan ultrasound probe can be used: (1) transverse scan; (2) longitudinal scan; and (3) axial scan.

FIG. 19 illustrates three different orientations in which the B-scan ultrasound probe can be used: (1) transverse scan; (2) longitudinal scan; and (3) axial scan. An appropriate marking can be provided on the ultrasound probe, as described below.

In a transverse scan, the ultrasound probe can be oriented tangentially to the limbus, with the probe marker pointing superiorly for vertical scans and oblique scans or nasally for horizontal scans. A transverse scan can be helpful to determine the lateral extent of a lesion.

In a longitudinal scan, the ultrasound probe can be oriented perpendicular to the limbus with the probe marker pointing to the center of the cornea. The scanned meridian can be designated by the clock hour opposite of where the marker is placed. A longitudinal scan can be used to determine the length (anterior to posterior) of the lesion or to identify the insertion of membranes. The imaging of longitudinal scans can always display the anterior eye superiorly and the posterior eye inferiorly.

In an axial scan, the ultrasound probe can be placed on the center of the cornea, with the patient looking straight ahead. Although this can result in poorer resolution of scans due to imaging through the dense media of the natural lens, axial scans can be useful for locating lesions in the posterior pole and determining where lesions are in relation to anatomical markers such as the optic nerve and macula. Axial scans can be done horizontally, vertically or obliquely.

Numbered List of Certain Illustrative Non-Limiting Aspects of the Disclosure:

Aspect 1. A health monitoring system for assessing a health condition of a patient via an image of an eye of the patient, the system comprising:
a fundus camera, for imaging the eye of the patient;
a camera positioning member, coupled to the camera, to position the camera with respect to the patient;
a patient positioning fixture, including one or more patient positioning features to position a corresponding particular portion of the patient at a desired location with respect to the patient positioning fixture; and
processor circuitry, coupled to control the camera, the camera positioning member, and the patient positioning fixture using programmed instructions performed by the processor circuitry, and for at least one of storing or image-processing images of the eye of the patient to provide a diagnostic indicator of the health condition of the patient.

Aspect 2. The system of Aspect 1, in which the patient positioning fixture includes an articulating arm, controllable by the processor circuitry to position a corresponding particular portion of the patient at a desired location with respect to the patient positioning fixture.

Aspect 3. The system of any of Aspects 1 or 2, wherein the patient positioning feature includes a patient-specific customized shape.

Aspect 4. The system of any of Aspects 1 through 3, wherein the patient positioning fixture includes an eyewear device including one or more poke-yoke features, one or more kinematic pins, one or more optical transponders, or one or more mating or other alignment features for aligning a position of an eye of the patient for imaging using the camera.

Aspect 5. The system of any of Aspects 1 through 4, comprising an eyewear device that includes at least one of an intraocular pressure (IOP) sensor, a humidity sensor, or a proximity sensor.

Aspect 6. The system of any of Aspects 1 through 5, comprising an eyewear device that includes a light source to illuminate the eye for imaging by the camera.

Aspect 7. The system of any of Aspects 1 through 6, comprising an eye positioning fixture that is wearable by the patient.

Aspect 8. The system of any of Aspects 1 through 7, comprising the processor circuitry including or coupled to at least one or local or remote image-processing componentry for at least one of image-parsing, image-stitching, or image analysis.

Aspect 9. The system of any of Aspects 1 through 8, comprising a biometric reader or other patient access control device to control at least one of assigning or assigning eye images or other data associated with a particular patient.

Aspect 10. The system of any of Aspects 1 through 9, wherein at least the camera positioning member is included in or coupled to patient head-fixation member configured to be head-worn by the patient.

Aspect 11. The system of any of Aspects 1 through 10, in which the camera positioning fixture includes an articulating arm, controllable by the processor circuitry to position the camera for movements through a range of positions over which multiple images are captured and stitched together to create a composite image permitting a view angle of at least 200 degrees of at least one of a peripheral or other vasculature, a fovea, a macula, a retina, or an optic nerve of the eye.

Aspect 12. The system of any of Aspects 1 through 11, comprising an eyewear device that includes a humidification outlet to provide humidity to the eye of the patient to treat dry eye.

Aspect 13. The system of any of Aspects 1 through 12, comprising an eyewear device that includes a medicament dispenser to dispense a liquid eye medicament into the eye of the patient.

Aspect 14. The system of any of Aspects 1 through 13, wherein the processor circuitry includes or is coupled to a machine learning (ML) model trained for positioning at least one of the camera or the patient with respect to the other.

Aspect 15. The system of any of Aspects 1 through 14, wherein the processor circuitry includes or is coupled to a machine learning (ML) model trained for image-processing of the images to identify a feature or anomaly in the image of the eye of the patient for use in providing a diagnostic indicator of the health condition of the patient.

Aspect 16. The system of any of Aspects 1 through 15, wherein the processor circuitry includes or is coupled to a machine learning (ML) model trained for image-processing of the images to identify a feature or anomaly in the image of the eye of the patient for use in providing a diagnostic indicator of the health condition of the patient, wherein the processor is capable of tagging the identified feature or anomaly using diagnostic data provided by a clinician or other evaluator of the images.

Aspect 17. The system of any of Aspects 1 through 16, wherein the processor circuitry includes video image processing rheology software configured to analyze fluid flow through vasculature of the eye of the patient using video images over a biologically appropriate sample period to provide a race and environment independent indication of infection or other diagnostic indicator of the health condition of the patient.

Aspect 18. The system of any of Aspects 1 through 17, comprising a telescoping mounting fixture to which at least one of the camera positioning member or the patient positioning fixture is attachable.

Aspect 19. The system of any of Aspects 1 through 18, comprising a bed-attachable mounting support fixture to which at least one of the camera positioning member or the patient positioning fixture is attachable.

Aspect 20. The system of any of Aspects 1 through 19, comprising a formed infant or toddler support liner shaped to stabilize an infant or toddler laying thereupon.

Aspect 21. The system of any of Aspects 1 through 20, comprising a wheelchair compatible mounting support fixture to which at least one of the camera positioning member or the patient positioning fixture is attachable to position at least one of the camera or the patient with respect to the other such that the camera is positionable at eye-level to a patient sitting on a wheelchair.

Aspect 22. The system of any of Aspects 1 through 21, comprising a vest, headgear, helmet, or other wearable mounting support fixture to which at least one of the camera positioning member or the patient positioning fixture is attachable.

Aspect 23. The system of any of Aspects 1 through 22, comprising a kiosk sized and shaped to accommodate positioning of the patient therein, the kiosk including the camera positioning member, the camera, and the patient positioning fixture.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An eye imaging system, comprising:
a head-wearable eye imager positioning helmet, including:
a conformable interior head liner arranged to conformally fit about a head of a patient;
an outer shell; and
an eye imager fixture, attachable to the outer shell of the helmet, the fixture including an eye imager positioner to permit the patient to self-position the eye imager with respect to an eye of the patient for acquiring one or more eye images.

2. The system of claim 1, wherein the eye imager fixture includes:
a mobile phone or camera holder, including a receptacle that is sized and shaped to receive and carry a mobile phone or camera; and
a patient eye socket conformable camera guide fixture, included in or coupled to the mobile phone or camera holder, arranged to permit the patient to self-position a camera of the mobile phone or the camera with respect to the eye of the patient to take an image of the eye of the patient.

3. The system of claim 2, wherein the patient eye socket conformable camera guide fixture is coupled to the mobile phone holder via a ball-joint to seat the patient eye socket conformable camera guide fixture against and conforming to the patient eye socket.

4. An eye imaging system, comprising:
a imaging device holder, including a receptacle that is sized and shaped to receive and carry an imaging device, and
a patient eye socket conformable imaging device guide fixture, included in or coupled to the imaging device holder, arranged to position the imaging device with respect to a patient eye socket associated with an eye of a patient to take an image of the eye of the patient.

5. The system of claim 4, wherein the patient eye socket conformable imaging device guide fixture is included in or coupled to a mobile phone holder that is included in the imaging device holder to seat the patient eye socket conformable imaging device guide fixture against and conforming to the patient eye socket.

6. The system of claim 4, wherein the imaging device is attached to a head-wearable eye imager positioning helmet to allow the patient to seat the patient eye socket conformable imaging device guide fixture against and conforming to the patient eye socket.

7. An eye imaging system, comprising:
a patient eye socket conformable imager guide fixture, arranged to position an eye imager with respect to an eye of a patient to take an image of the eye of the patient; and
wherein the patient eye socket conformable imager guide fixture is adapted to be coupled to an eye imager via a ball-joint to allow the patient to employ the ball-joint to seat the patient eye socket conformable imager guide fixture against and conforming to the patient eye socket.

8. The system of claim 7, further comprising an eye imager.

9. The system of claim 8, wherein the eye imager includes a mobile phone including a mobile phone camera, and wherein the patient eye socket conformable imager guide fixture is adapted to be coupled to the mobile phone.

10. The system of claim 8, wherein the eye imager includes a fundus camera, and wherein the eye socket conformable imager guide fixture is adapted to be coupled to the fundus camera.

11. The system of claim 8, wherein the eye imager includes an ultrasound imaging transducer.

12. The system of claim 11, further comprising a conformable gel pack locatable against the eye of the patient and between the ultrasound imaging transducer and the eye of the patient, to provide an acoustic impedance for performing ultrasound imaging of the eye.

13. The system of claim 11, further comprising a gel dispenser locatable for dispensing ultrasound impedance-matching gel against the eye of the patient and between the ultrasound imaging transducer and the eye of the patient, to provide an acoustic impedance for performing ultrasound imaging of the eye.

14. An eye imaging system, comprising:

a head-wearable eye imager positioning headpiece, wearable on most superior portion of a head of a patient and including:

an eye imager fixture, attachable to the headpiece, the fixture including an eye imager positioner to position the eye imager with respect to an eye of the patient for acquiring one or more eye images; and an impact detection sensor, configured to detect an impact to the head of the patient; and processing circuitry, configured to image-process image data from the eye imager, including qualifying the image data when the impact sensor indicates an impact to the head of a patient meeting at least one criterion.

15. The system of claim 14, wherein the eye imager fixture includes:

a mobile phone holder, including a receptacle that is sized and shaped to receive and carry a mobile phone; and a patient eye socket conformable camera guide fixture, included in or coupled to the mobile phone holder, arranged to position a camera of the mobile phone with respect to the eye of the patient to take an image of the eye of the patient.

16. The system of claim 15, wherein the patient eye socket conformable camera guide fixture is coupled to the mobile phone holder via a ball-joint to allow the patient to seat the patient eye socket conformable camera guide fixture against and conforming to the patient eye socket.

17. The system of claim 14, wherein the eye imager includes an ultrasound imaging transducer.

18. The system of claim 17, further comprising at least one of a gel dispenser or a conformable gel pack locatable toward or against the eye of the patient and between the ultrasound imaging transducer and the eye of the patient, to provide an acoustic impedance for performing ultrasound imaging of the eye.

19. The system of claim 1, wherein the helmet includes one or more fiducials arranged to provide a geometric coordinate system or reference with respect to at least a portion of the head of the patient when the patient is wearing the helmet.

20. The system of claim 1, wherein the patient is a specific patient, and wherein the conformable interior head liner is pre-shaped to be customized for the specific patient to conform to fit about the head of the specific patient.

* * * * *